(12) United States Patent
Nankervis

(10) Patent No.: US 9,175,259 B2
(45) Date of Patent: Nov. 3, 2015

(54) METHOD OF LOADING AND DISTRIBUTING CELLS IN A BIOREACTOR OF A CELL EXPANSION SYSTEM

(71) Applicant: Terumo BCT, Inc., Lakewood, CO (US)

(72) Inventor: Brian J. Nankervis, Thornton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 5 days.

(21) Appl. No.: 13/971,500

(22) Filed: Aug. 20, 2013

(65) Prior Publication Data

US 2014/0051162 A1    Feb. 20, 2014

Related U.S. Application Data

(60) Provisional application No. 61/691,193, filed on Aug. 20, 2012.

(51) Int. Cl.
| | |
|---|---|
| *C12N 5/00* | (2006.01) |
| *C12M 3/04* | (2006.01) |
| *C12M 3/00* | (2006.01) |
| *C12M 3/02* | (2006.01) |
| *C12M 1/00* | (2006.01) |
| *C12M 1/12* | (2006.01) |
| *C12M 1/34* | (2006.01) |
| *C12M 1/24* | (2006.01) |

(52) U.S. Cl.
CPC ............... *C12N 5/00* (2013.01); *C12N 5/0081* (2013.01); *C12M 3/00* (2013.01); *C12M 3/02* (2013.01); *C12M 23/08* (2013.01); *C12M 25/12* (2013.01); *C12M 27/10* (2013.01); *C12M 41/00* (2013.01); *C12M 47/04* (2013.01)

(58) Field of Classification Search
None
See application file for complete search history.

(56) References Cited

U.S. PATENT DOCUMENTS

| | | |
|---|---|---|
| 5,162,225 A | 11/1992 | Sager et al. |
| 6,001,585 A | 12/1999 | Gramer |
| 2008/0220523 A1* | 9/2008 | Antwiler .................. 435/394 |
| 2011/0159584 A1* | 6/2011 | Gibbons et al. ............ 435/325 |
| 2012/0086657 A1 | 4/2012 | Stanton, IV et al. |
| 2012/0088224 A1 | 4/2012 | DiLorenzo et al. |

FOREIGN PATENT DOCUMENTS

| | | |
|---|---|---|
| WO | 86/02378 A1 | 4/1986 |
| WO | 00/12676 A2 | 3/2000 |
| WO | 2008/109668 A2 | 9/2008 |
| WO | 2008/109674 A2 | 9/2008 |

OTHER PUBLICATIONS

International Search Report and Written Opinion, PCT/US2013/055831, Nov. 7, 2013.

* cited by examiner

*Primary Examiner* — Allison Fox
*Assistant Examiner* — Susan E Fernandez
(74) *Attorney, Agent, or Firm* — René A. Pereyra; Elizabeth J. Reagan; John R. Merkling

(57) ABSTRACT

One or more embodiments are described directed to a method and system for loading and distributing cells in a bioreactor of a cell expansion system. Accordingly, embodiments include methods and systems that may provide for adding a plurality of cells to a fluid within a bioreactor of the cell expansion system. A first percentage of the plurality of cells is allowed to settle in the bioreactor and a second percentage of the plurality of cells is allowed to settle outside of the bioreactor. The first percentage of cells is then expanded in the bioreactor. The second percentage of cells is wasted.

8 Claims, 22 Drawing Sheets

METHOD OF LOADING AND DISTRIBUTING CELLS IN A BIOREACTOR OF A CELL EXPANSION SYSTEM

CROSS-REFERENCE TO RELATED PATENT APPLICATIONS

This patent application claims priority to U.S. Provisional Patent Application No. 61/691,193, entitled METHOD OF LOADING AND DISTRIBUTING CELLS IN A BIOREACTOR OF A CELL EXPANSION SYSTEM, filed on Aug. 20, 2012, and hereby incorporated by references in its entirety as if set forth herein in full.

BACKGROUND

CESs are used to expand and differentiate cells. Cell expansion systems are known in the art. For example, U.S. Pat. Nos. 5,162,225 and 6,001,585 generally describe cell expansion systems designed for cell expansion.

The potential use of stem cells in a variety of treatments and therapies has achieved particular attention. Cell expansion systems can be used to expand, e.g., grow, stem cells, as well as other types of cells, such as bone marrow cells. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems include one or more compartments for expanding the cells, such as a cell growth chamber, also referred to herein as a "bioreactor." In order to expand cells, an initial volume of cells is typically loaded into, and distributed within, the bioreactor. Accordingly, there is a need for a method of loading and distributing cells in a bioreactor associated with a cell expansion system. The present disclosure addresses this and other needs.

Embodiments of the present invention have been made in light of these and other considerations. However, the relatively specific problems discussed above do not limit the applicability of the embodiments of the present invention to solving other problems.

SUMMARY

The summary is provided to introduce aspects of some embodiments of the present invention in a simplified form, and is not intended to identify key or essential elements of the claimed invention, nor is it intended to limit the scope of the claims.

It is to be understood that the present invention may include a variety of different versions or embodiments, and this Summary is not meant to be limiting or all-inclusive. This Summary provides some general descriptions of features that may be included in embodiments, and also include some more specific descriptions of other features that may be included in other embodiments.

One or more embodiments are generally directed to a method and system for loading and distributing cells in a bioreactor of a cell expansion system. Accordingly, embodiments include methods that may provide for adding a plurality of cells to a fluid circulating at a first rate within a bioreactor of the cell expansion system. The circulation rate of the fluid is maintained at a first rate for a predetermined period of time to obtain a desired cell concentration in the fluid. After the desired cell concentration has been achieved, the circulation rate of the fluid is reduced to a reduced rate that is less than the first rate. A first percentage of the plurality of cells is allowed to settle in the bioreactor and a second percentage of the plurality of cells is allowed to settle outside of the bioreactor. The first percentage of cells is then expanded in the bioreactor. The second percentage of cells is wasted. While the circulation rate is maintained at the first rate, embodiments may provide for rotating the bioreactor around a rotational axis from a first orientation to a second orientation, pausing the bioreactor at the second orientation for a first period of time, rotating the bioreactor back around the rotational axis to the first orientation, and then pausing the bioreactor back at the first orientation for a second period of time.

Embodiments of the present invention are also directed to a system for expanding cells. The embodiments may include a bioreactor reactor comprising a first fluid flow path having at least opposing ends, a first opposing end of said first fluid flow path fluidly associated with a first port of a hollow fiber membrane and a second end of said first fluid flow path fluidly associated with a second port of the hollow fiber membrane, wherein said first fluid flow path comprises an intracapillary portion of said hollow fiber membrane. The embodiments may also include a fluid inlet path fluidly associated with said first fluid flow path, wherein the plurality of cells are introduced into the first fluid flow path through the first fluid inlet path. A first pump for circulating fluid in the first fluid flow path of the bioreactor may also be included in the embodiments. The embodiments may further include a controller for controlling operation of the first pump, wherein the controller is configured to control the pump to circulate a fluid at a first rate within the first fluid flow path, maintain the circulation rate of the fluid at the first rate for a predetermined period of time to obtain a desired cell concentration in the fluid, after the desired cell concentration has been achieved, reduce the circulation rate of the fluid to a reduced rate that is less than the first rate to allow a first percentage of the plurality of cells to settle in the bioreactor and a second percentage of the plurality of cells to settle outside of the bioreactor, and circulate a fluid with growth media for expanding the first percentage of cells in the bioreactor and removing most of the second percentage of cells from the first fluid flow path.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and is understood by those of ordinary skill in the art to encompass obvious improvements and modifications thereto.

Additional advantages of the embodiments presented herein will become readily apparent from the following discussion, particularly when taken together with the accompanying drawings.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below. The present disclosure is generally directed to a method for distributing a plurality of cells in a bioreactor of a cell expansion system. As described below, a method of distributing cells within a bioreactor may include loading cells into the bioreactor, rotating the bioreactor, and holding the bioreactor still at certain orientations.

Figure 1A:
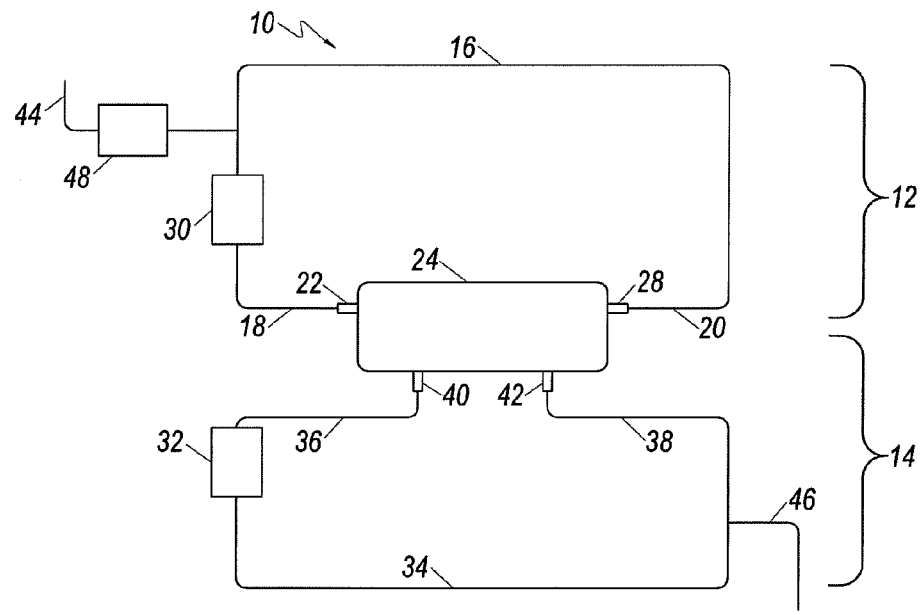
FIG. 1A depicts one embodiment of a cell expansion system (CES)

A schematic of an example cell expansion system (CES) is depicted in FIG. 1A. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"). Specifically, opposing end 18 is fluidly associated with a first inlet 22 of cell growth chamber 24, and opposing end 20 is fluidly associated with first outlet 28 of cell growth chamber 24. Fluid in first circulation path 12 flows through the interior of hollow fibers of hollow fiber membrane 50 disposed in cell growth chamber 24 (cell growth chambers and hollow fiber membranes are described in more detail infra). Further, first fluid flow controller 30 is operably connected to first fluid flow path 16, and controls the flow of fluid in first circulation path 12.

Second fluid circulation path 14 includes second fluid flow path 34, cell growth chamber 24, and a second fluid flow controller 32. The second fluid flow path 34 has at least opposing ends 36 and 38. Opposing ends 36 and 38 of second fluid flow path 34 are fluidly associated with inlet port 40 and outlet port 42 respectively of cell growth chamber 24. Fluid flowing through cell growth chamber 24 is in contact with the outside of hollow fiber membrane in the cell growth chamber 24. Second fluid circulation path 14 is operably connected to second fluid flow controller 32.

First and second fluid circulation paths 12 and 14 are thus separated in cell growth chamber 24 by a hollow fiber membrane. Fluid in first fluid circulation path 12 flows through the intracapillary ("IC") space of the hollow fibers in the cell growth chamber. First circulation path 12 is thus referred to as the "IC loop." Fluid in second circulation path 14 flows through the extracapillary ("EC") space in the cell growth chamber. Second fluid circulation path 14 is thus referred to as the "EC loop." Fluid in first fluid circulation path 12 can flow in either a co-current or counter-current direction with respect to flow of fluid in second fluid circulation path 14.

Fluid inlet path 44 is fluidly associated with first fluid circulation path 12. Fluid inlet path 44 allows fluid into first fluid circulation path 12, while fluid outlet path 46 allows fluid to leave CES 10. Third fluid flow controller 48 is operably associated with fluid inlet path 44. Alternatively, third fluid flow controller 48 can alternatively be associated with fluid outlet path 46.

Fluid flow controllers as used herein can be a pump, valve, clamp, or combination thereof. Multiple pumps, valves, and clamps can be arranged in any combination. In various embodiments, the fluid flow controller is or includes a peristaltic pump. In further embodiments, fluid circulation paths, inlet ports, and outlet ports can be constructed of tubing of any material.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Generally, any kind of fluid, including buffers, protein containing fluid, and cell-containing fluid can flow through the various circulations paths, inlet paths, and outlet paths. As used herein, "fluid," "media," and "fluid media" are used interchangeably.

Figure 1D:
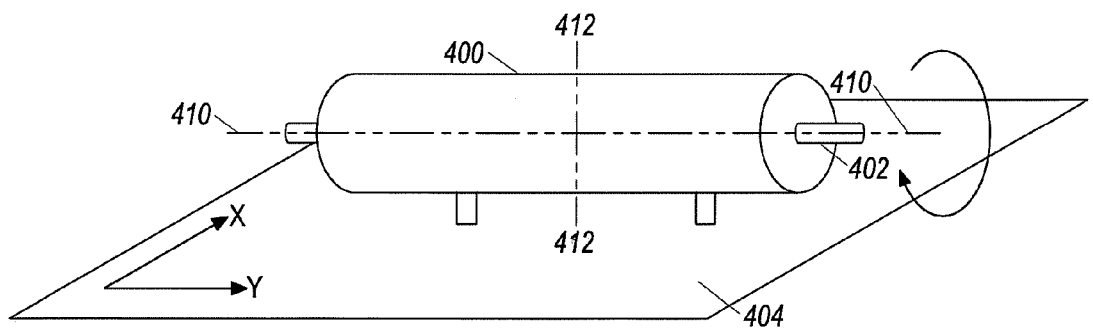
FIG. 1D depicts a rocking device for moving a cell growth chamber rotationally or laterally during operation of the CES.
Figure 1B:
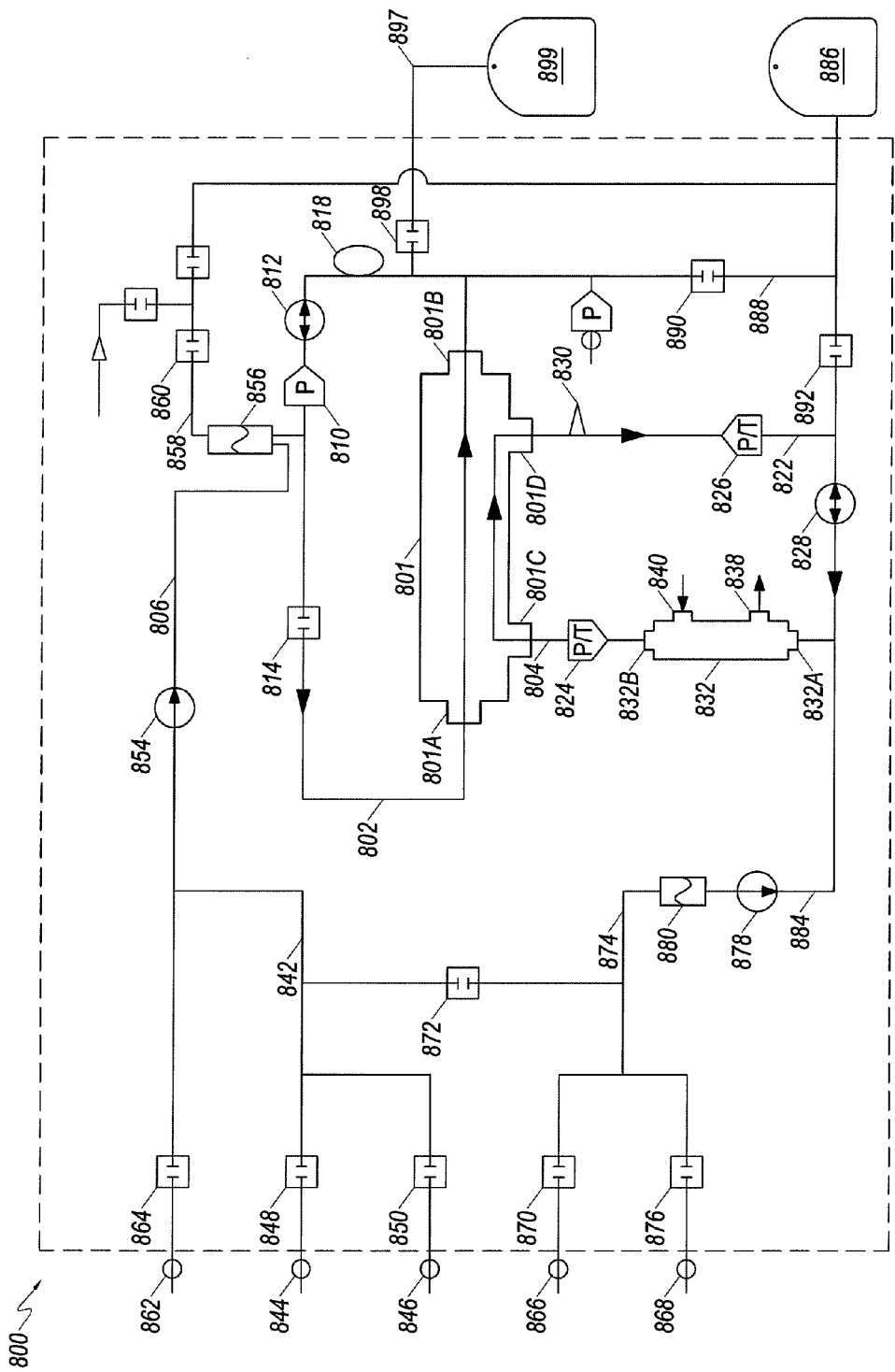
FIG. 1B depicts another embodiment of a CES.

FIG. 1B depicts a more detailed cell expansion system 800. CES 800 includes a first fluid circulation path 802 (also referred to as the "intracapillary loop" or "IC loop") and second fluid circulation path 804 (also referred to as the "extracapillary loop" or "EC loop"). First fluid flow path 806 is fluidly associated with cell growth chamber 801 to form first fluid circulation path 802. Fluid flows into cell growth chamber 801 through IC inlet port 801A, through hollow fibers in cell growth chamber 801, and exits via IC outlet port 801B. Pressure sensor 810 measures the pressure of media leaving cell growth chamber 801. In addition to pressure, sensor 810 may in embodiments also be a temperature sensor that detects the media pressure and temperature during operation. Media flows through IC circulation pump 812 which can be used to control the rate of media flow. IC circulation pump 812 may pump the fluid in a first direction or second direction opposite the first direction. Exit port 801B can be used as an inlet in the reverse direction. Media entering the IC loop may enter through valve 814. As those skilled in the art will appreciate, additional valves and/or other devices can be placed at various locations to isolate and/or measure characteristics of the media along portions of the fluid paths. Accordingly, it is to be understood that the schematic shown represents one possible configuration for various elements of the CES 800 and modifications to the schematic shown are within the scope of the one or more present embodiments.

With regard to the IC loop, samples of media can be obtained from sample coil 818 during operation. Media then returns to IC inlet port 801A to complete fluid circulation path 802. Cells grown/expanded in cell growth chamber 801 can be flushed out of cell growth chamber 801 into harvest bag 899 through valve 898 and line 897. Alternatively, when valve 898 is closed, the cells may be redistributed within chamber 801 for further growth.

Fluid in second fluid circulation path 804 enters cell growth chamber 801 via EC inlet port 801C, and leaves cell growth chamber 801 via EC outlet port 801D. Media in the EC loop is in contact with the outside of the hollow fibers in the cell growth chamber 801, thereby allowing diffusion of small molecules into and out of the hollow fibers that may be within chamber 801.

Pressure/temperature sensor 824 disposed in the second fluid circulation path 804 allows the pressure and temperature of media to be measured before the media enters the EC space of the cell growth chamber 801. Sensor 826 allows the pressure and temperature of media in the second fluid circulation path 804 to be measured after it leaves the cell growth chamber 801. With regard to the EC loop, samples of media can be obtained from sample port 830 or a sample coil during operation.

After leaving EC outlet port 801D of cell growth chamber 801, fluid in second fluid circulation path 804 passes through EC circulation pump 828 to gas transfer module 832. EC circulation pump 828 may also pump the fluid in opposing directions. Second fluid flow path 822 is fluidly associated with gas transfer module 832 via an inlet port 832A and an outlet port 832B of gas transfer module 832. In operation, fluid media flows into gas transfer module 832 via inlet port 832A, and exits gas transfer module 832 via outlet port 832B. Gas transfer module 832 adds oxygen to and removes bubbles from media in the CES 800. In various embodiments, media in second fluid circulation path 804 is in equilibrium with gas entering gas transfer module 832. The gas transfer module 832 can be any appropriately sized device known in the art and useful for oxygenation or gas transfer. Air or gas flows into gas transfer module 832 via filter 840 and out of oxygenator or gas transfer device 832 through filter 838. Filters 838 and 840 reduce or prevent contamination of oxygenator 832 and associated media. Air or gas purged from the CES 800 during portions of a priming sequence can vent to the atmosphere via the gas transfer module 832.

In the configuration depicted for CES 800, fluid media in first fluid circulation path 802 and second fluid circulation path 804 flows through cell growth chamber 801 in the same direction (a co-current configuration). The CES 800 can also be configured to flow in a counter-current conformation.

In accordance with at least one embodiment, media, including cells (from a source such as a cell container, e.g. a bag) can be attached at attachment point 862, and fluid media from a media source can be attached at attachment point 846. The cells and media can be introduced into first fluid circulation path 802 via first fluid flow path 806. Attachment point 862 is fluidly associated with the first fluid flow path 806 via valve 864, and attachment point 846 is fluidly associated with the first fluid flow path 806 via valve 850. A reagent source may be fluidly connected to point 844 and be associated with fluid inlet path 842 via valve 848, or second fluid inlet path 874 via valves 848 and 872.

Air removal chamber (ARC) 856 is fluidly associated with first circulation path 802. The air removal chamber 856 may include one or more sensors including an upper sensor and lower sensor to detect air, a lack of fluid, and/or a gas/fluid interface, e.g., an air/fluid interface, at certain measuring positions within the air removal chamber 856. For example, ultrasonic sensors may be used near the bottom and/or near the top of the air removal chamber 856 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 800 during portions of the priming sequence or other protocols can vent to the atmosphere out air valve 860 via line 858 that is fluidly associated with air removal chamber 856.

An EC media source may be attached to EC media attachment point 868 and a wash solution source may be attached to wash solution attachment point 866, to add EC media and/or wash solution to either the first or second fluid flow path. Attachment point 866 may be fluidly associated with valve 870 that is fluidly associated with first fluid circulation path 802 via valve 872 and first fluid inlet path 842. Alternatively, attachment point 866 can be fluidly associated with second fluid circulation path 804 via second fluid inlet path 874 and second fluid flow path 884 by opening valve 870 and closing valve 872. Likewise, attachment point 868 is fluidly associated with valve 876 that may be fluidly associated with first fluid circulation path 802 via first fluid inlet path 842 and valve 872. Alternatively, fluid container 868 may be fluidly associated with second fluid inlet path 874 by opening valve 876 and closing valve distribution 872.

In the IC loop, fluid may be initially advanced by the IC inlet pump 854. In the EC loop, fluid is initially advanced by the EC inlet pump 878. An air detector 880, such as an ultrasonic sensor, may also be associated with the EC inlet path 884.

In at least one embodiment, first and second fluid circulation paths 802 and 804 are connected to waste line 888. When valve 890 is opened, IC media can flow through waste line 888 and to waste bag 886. Likewise, when valve 892 is opened, EC media can flow to waste bag 886.

After cells have been grown in cell growth chamber 801, they may be harvested via cell harvest path 897. Here, cells from cell growth chamber 801 can be harvested by pumping the IC media containing the cells through cell harvest path 897, with valve 898 open, into cell harvest bag 899.

Figure 1C:
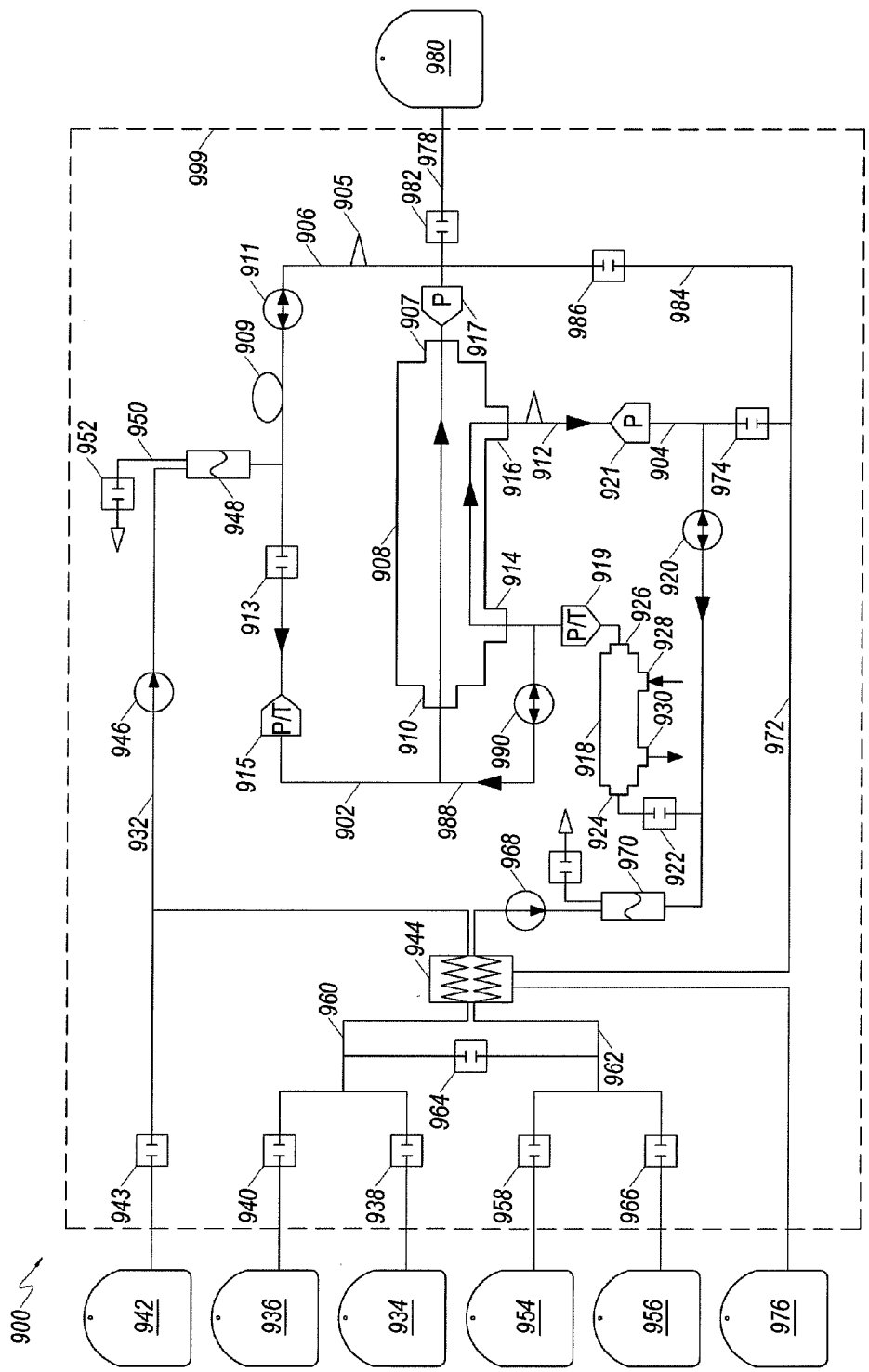
FIG. 1C depicts yet another embodiment of a CES.

Various components of the CES 800 can be contained or housed within a machine or housing, such as a cell expansion machine, wherein the machine maintains cells and media at a predetermined temperature. It is further noted that in embodiments, components of CES 800 may be combined with other CES such as CES 10 (FIG. 1A) or CES 900 (FIG. 1C). In other embodiments, a CES may include fewer components than shown in FIGS. 1A-C and still be within the scope of the present disclosure.

FIG. 1C depicts another embodiment of a CES. CES 900 includes first fluid circulation path 902 (also referred to as the "intracapillary (IC) loop") and second fluid circulation path 904 (also referred to as the "extracapillary loop" or "EC loop").

First fluid flow path 906 is fluidly associated with cell growth chamber 908 to form first fluid circulation path 902. Fluid flows into cell growth chamber 908 through inlet port 910, through hollow fibers in cell growth chamber 908, and exits via outlet port 907. Pressure gauge 917 measures the pressure of media leaving cell growth chamber 908. Media flows through valve 913 and pump 911, which can be used to control the rate of media flow. Samples of media can be obtained from sample port 905 or sample coil 909 during operation. Pressure/temperature gauge 915 disposed in first fluid circulation path allows detection of media pressure and temperature during operation. Media then returns to inlet port 910 to complete fluid circulation path 902. Cells expanded in cell growth chamber 908 can be flushed out of cell growth chamber 908 or redistributed within hollow fibers for further growth.

Second fluid circulation path 904 includes second fluid flow path 912 that is fluidly associated with cell growth chamber 908 in a loop. Fluid in second fluid circulation path 904 enters cell growth chamber 908 via inlet port 914, and leaves cell growth chamber 908 via outlet port 916. Media is in contact with the outside of the hollow fibers in the cell growth chamber 908, allowing diffusion of small molecules into and out of the hollow fibers.

Pressure/temperature gauge 919 disposed in the second circulation path allows the pressure and temperature of media to be measured before the media enters the EC space of the cell growth chamber 908. Pressure gauge 921 allows the pressure of media in the second circulation path to be measured after it leaves the cell growth chamber.

After leaving outlet port 916 of cell growth chamber 908, fluid in second fluid circulation path 904 passes through pump 920 and valve 922 to oxygenator 918. Second fluid flow path 912 is fluidly associated with oxygenator 918 via oxygenator inlet port 924 and oxygenator outlet port 926. In operation, fluid media flows into oxygenator 918 via oxygenator inlet port 924, and exits oxygenator 918 via oxygenator outlet port 926.

Oxygenator 918 adds oxygen to media in the CES. In various embodiments, media in second fluid circulation path 904 is in equilibrium with gas entering oxygenator. The oxygenator can be any oxygenator known in the art. Gas flows into oxygenator 918 via filter 928 and out of oxygenator 918 through filter 930. Filters 928 and 930 reduce or prevent contamination of oxygenator 918 and associated media.

In the configuration depicted for CES 900, fluid media in first circulation path 902 and second circulation path 904 flow through cell growth chamber 908 in the same direction (a co-current configuration). Those of skill in the art will recognize that CES 900 can also be configured in a counter-current conformation. Those of skill in the art will recognize that the respective inlet and outlet ports can be disposed in the cell growth chamber at any location.

Cells and fluid media can be introduced to fluid circulation path 902 via first fluid inlet path 932. Fluid container 934 and fluid container 936 are fluidly associated with first fluid inlet path 932 via valves 938 and 940 respectively. Likewise, cell container 942 is fluidly associated with first fluid circulation path 902 via valve 943. Cells and fluid proceed through heat exchanger 944, pump 946, and into drip chamber 948. Drip chamber 948 is fluidly associated with first circulation path 902. Overflow from drip chamber 948 can flow out of drip chamber 948 from overflow line 950 via valve 952.

Additional fluid can be added to first or second fluid circulation paths 902 and 904 from fluid container 954 and fluid container 956. Fluid container 954 is fluidly associated with valve 958 which is fluidly associated with first fluid circulation path 902 via first fluid inlet path 960. First fluid flow path includes valve 964. Alternatively, fluid container 954 is fluidly associated with second fluid inlet path 962. Likewise, fluid container 956 is fluidly associated with valve 966, which is fluidly associated with first fluid circulation path 902 via first fluid inlet path 960. Alternatively, fluid container 956 is fluidly associated with second fluid inlet path 962.

Second fluid inlet path 962 is configured to allow fluid to flow through pump 968 before entering drip chamber 970. Second fluid inlet path 962 continues to second fluid circulation path 904. Overflow fluid can flow out via overflow line 972 through valve 974 to waste container 976.

Cells can be harvested via cell harvest path 978. Cells from cell growth chamber 908 can be harvested by pumping media containing the cells through cell harvest path 978 to cell harvest bag 980.

First and second fluid circulation paths 902 and 904 are connected by connector path 984. When valve 986 is opened, media can flow through connector path 984 between first and second circulation paths 902 and 904. Likewise, pump 990 can pump media through another connector path 988 between first and second fluid circulation paths 902 and 904.

Various components of the CES can be contained within incubator 999. Incubator 999 maintains cells and media at a constant temperature.

As will be recognized by those of skill in the art, any number of fluid containers (e.g. media bags) can be fluidly associated with the CES in any combination. It will further be noted that the location of the drip chamber, or sensors independent of the drip chamber, can be at any location in the CES before inlet port 910.

The CES can include additional components. For example, one or more pump loops (not shown) can be added at the location of peristaltic pumps on the CES. The pump loops may be made of polyurethane (PU) (available as Tygothane C-210A)). Alternatively, a cassette for organizing the tubing lines and which may also contain tubing loops for the peristaltic pumps may also be included as part of the disposable.

A detachable flow circuit (also referred to herein as a "detachable circulation module") may also be provided in some embodiments. The detachable flow circuit may be a portion of a cell expansion module configured to attach to a more permanent fixed portion of the CES. Generally, the fixed portions of the CES include peristaltic pumps. In various embodiments, the fixed portions of the CES can include valves and/or clamps.

The detachable flow circuit can include a first fluid flow path having at least two ends. The first end is configured to be fluidly associated with a first end of a cell growth chamber, and a second end of the first fluid flow path configured to fluidly associated with a second end of the cell growth chamber.

Likewise, the detachable flow circuit can include a second fluid flow path having at least two ends. Portions of the detachable flow circuit can be configured to be fluidly associated with an oxygenator and/or bioreactor. The detachable flow circuit can include a second fluid flow path that may be configured to fluidly associate with the oxygenator and cell growth chamber.

Figure 1E:
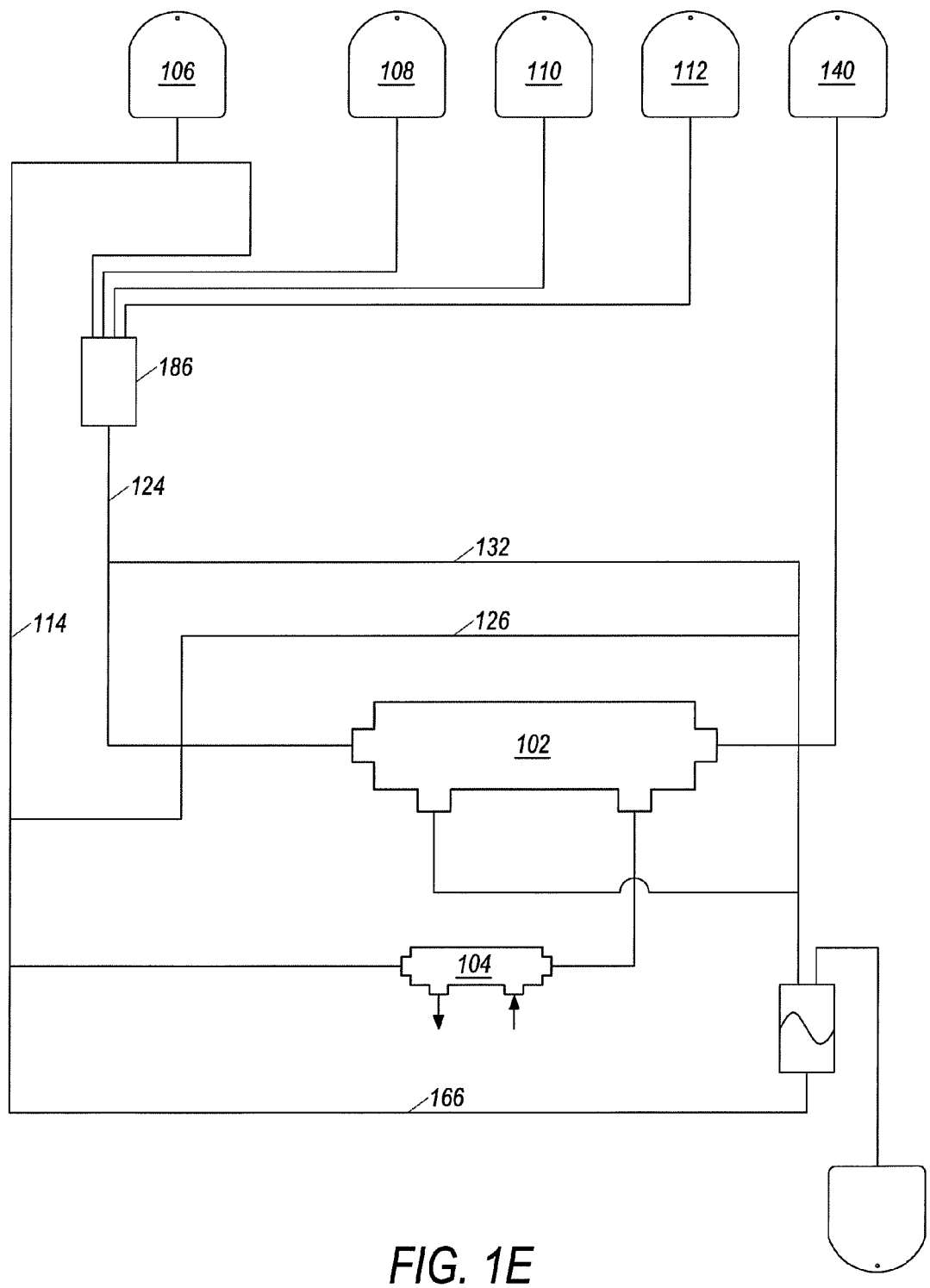
FIG. 1E depicts a detachable flow circuit for use with a CES.

In various embodiments, the detachable flow circuit may be detachably and disposably mounted to a fluid flow controller. The detachable flow circuit can include detachable fluid conduits (e.g. flexible tubing) that connects portions of the CES. With reference to FIG. 1E, the detachable flow circuit includes the tubing for first fluid circulation path 126, but without a pump. The detachable flow circuit can further include the tubing for flush line 132, without a valve. The detachable flow circuit can further include the tubing connecting first circulation path 126 to flush line 132, and first fluid inlet path 124. In various other permutations, the detachable flow circuit can include tubing that connects the media inlet bags 106 and 108, vent bag 110, and cell input bag 112 to drip chamber 186. The detachable flow circuit can also include tubing connecting cell harvest bag 140 to first circulation path 126.

Likewise, the detachable flow circuit can include tubing that makes up second circulation path 166. For example, the tubing can include tubing connecting oxygenator 104 to cell growth chamber 102, as well as drip chamber 186. The detachable flow circuit can also include fluid inlet path 114.

In further embodiments, the detachable flow circuit can include a cell growth chamber, oxygenator, as well as bags for containing media and cells. In various embodiments, the components can be connected together, or separate. Alternatively, detachable flow circuit can include one or more portions configured to attach to fluid flow controllers, such as valves, pumps, and combinations thereof. In variations where peristaltic pumps are used, the detachable circuit module can include a peristaltic loop configured to fit around a peristaltic portion of the tubing. In various embodiments, the peristaltic loop can be configured to be fluidly associated with the circulations paths, inlet paths, and outlet paths. The detachable flow circuit can be combined in a kit with instructions for its assembly or attachments to fluid flow controllers, such as pumps and valves.

Embodiments provide for using a number of different methods to introduce cells into bioreactors of CES. As described in greater detail below, embodiments include methods and systems that distribute cells in the bioreactor to promote consistent expansion of cells.

According to embodiments, cells can be grown ("expanded") in either the IC loop or the EC loop. Adherent and non-adherent suspension cells can be expanded. In one embodiment, the lumen of the cell growth chamber fibers can be coated with fibronectin. Divalent cation-free (e.g. calcium and magnesium-free) PBS is added to a CES system. After adherent cells are introduced into a cell growth chamber, e.g., chamber 24, 908, or 801 they are incubated for a sufficient time to adhere to the hollow fibers. IC and EC media are circulated to ensure sufficient nutrients are supplied to the cells.

The flow rate of the IC loop and EC loop can be adjusted to a specific value. In various embodiments, the flow rate of the IC loop and EC loops can be, independently set to, about 2, about 4, about 6, about 8, about 10, about 15, about 20, about 25, about 30, about 35, about 40, about 45, about 50, about 60, about 70, about 80, about 90, about 100, about 200, about 300, about 400 or about 500 mL/minute. In various embodiments, the flow rates for the IC circuit loop may be 10-20 mL/minute, and the flow rate of the EC circuit loop may be 20-30 mL per minute (allowing media to flow through an oxygenator and re-establish oxygen levels). Additional media may be pumped into the CES at a lower flow rate (e.g. 0.1 mL per minute in some embodiments) to replace media that evaporates through a gas exchange module(s) such as gas exchange/oxygenators 30, 918, or 832. In various embodiments, the EC loop removes cellular waste, and the IC loop includes growth factors in the media.

CES's may provide a great deal of flexibility in varying growth conditions and criteria. Cells can be kept in suspension in the IC loop by circulating media continuously. Alternatively, media circulation can be stopped, causing cells to settle. Fresh media can be added to the IC loop by ultrafiltration to accommodate excess volume without removing cells. EC media circulation allows for exchange of gas, nutrients, waste products, and addition of new media without removing cells.

Expanded cells can include adherent cells, non-adherent cells, or a co-culture of any combination of cells in the art.

In embodiments, to harvest adherent cells, the IC and EC media may be replaced with media that is free of divalent cations (e.g. divalent cation-free PBS). In one embodiment, trypsin may be loaded into a first circulation path, and allowed to incubate with adherent cells for a period of time (in some embodiments about 5 to about 10 minutes). The trypsin may then be flushed from the system. A shearing force may be applied to the cells by increasing the flow rate through cell growth chamber, and adherent cells that are released from the cell growth chamber may be pumped to a cell harvest bag.

When non-adherent cells are expanded, the cells can be flushed from the circulating IC circuit. Adherent cells remain in the cell growth chamber, while non-adherent cells are removed.

The CES can be used to perform a variety of cell expansion methods.

In one embodiment, a seeded population of cells can be expanded. Cells are introduced, or seeded, into the CES. In certain circumstances, the lumen of the hollow fibers can be conditioned to allow cell adhesion. Cells are then added to the cell growth chamber, and adherent cells adhere to the hollow fibers, while non-adherent cells (e.g. hematopoetic stem cells, or HSCs) do not adhere. The non-adherent cells can be flushed from the system. After incubation for a period of time, the adherent cells can be released and harvested.

Stem cells, progenitor cells, and fully differentiated cells can all be expanded.

The cell growth chamber of the cell expansion system in embodiments include a hollow fiber membrane comprised of a plurality of semi-permeable hollow fibers separating first and second fluid circulation paths.

Figure 2A:
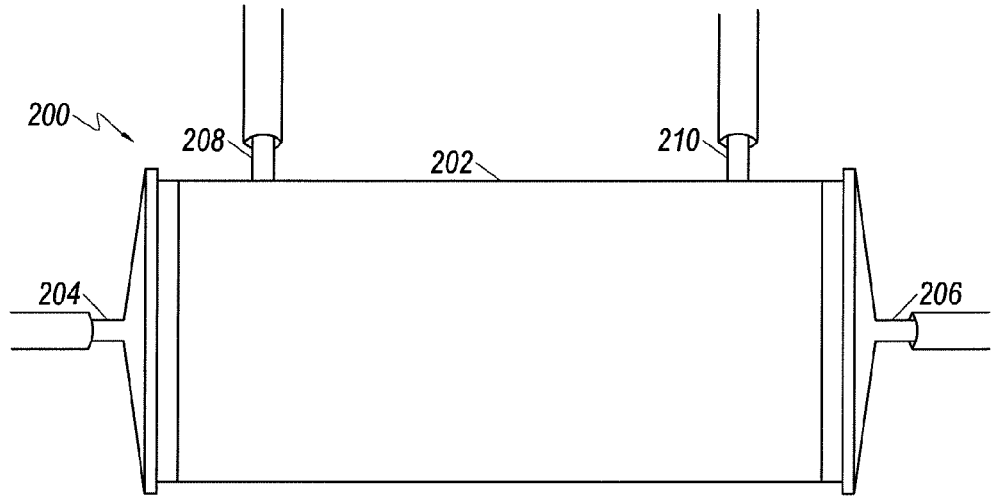
FIG. 2A depicts a side view of a hollow fiber cell growth chamber embodiment of a cell growth chamber.
Figure 2B:
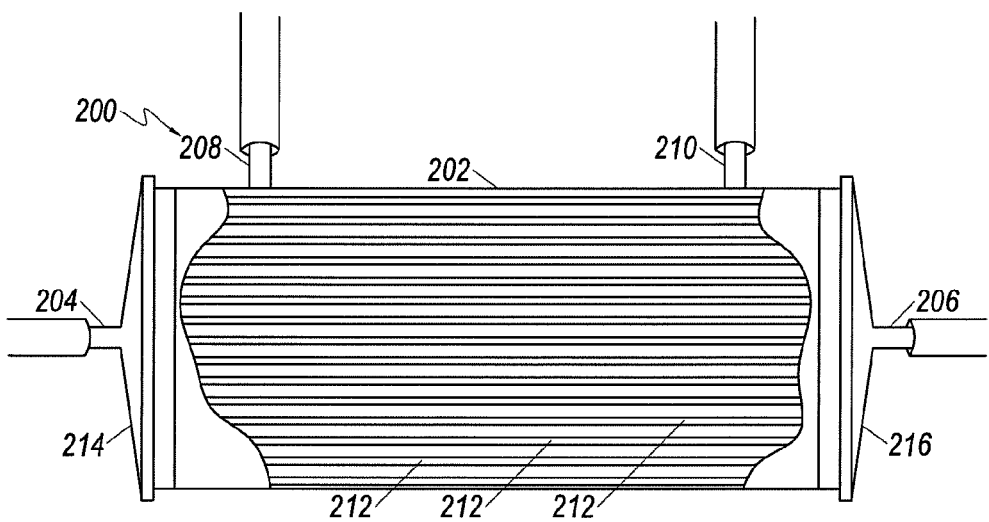
FIG. 2B depicts a cut-away side view of the hollow fiber cell growth chamber embodiment of FIG. 2A.

An embodiment of a cell growth chamber is depicted in FIGS. 2B and 2A, which depicts a cut-away and side view of a hollow fiber cell growth chamber 200. Cell growth chamber 200 is bounded by cell growth chamber housing 202. Cell growth chamber housing 202 further includes four openings, or ports: inlet port 204, outlet port 206, inlet port 208, and outlet port 210.

Fluid in the first circulation path enters cell growth chamber 200 through inlet port 204, passes into and through the intracapillary side of a plurality of hollow fibers (referred to in various embodiments as the intracapillary ("IC") side or "IC space" of a hollow fiber membrane), and out of cell growth chamber 200 through outlet port 206. The terms "hollow fiber," "hollow fiber capillary," and "capillary" are used interchangeably. A plurality of hollow fibers are collectively referred to as a "membrane." Fluid in the second circulation path flows in the cell growth chamber through inlet port 208, comes in contact with the outside of the hollow fibers (referred to as the "EC side" or "EC space" of the membrane), and exits cell growth chamber 200 via outlet port 210. Cells can be contained within the first circulation path or second circulation path, and can be on either the IC side or EC side of the membrane.

Although cell growth chamber housing 202 is depicted as cylindrical in shape, it can have any other shape known in the art. Cell growth chamber housing 202 can be made of any type of biocompatible polymeric material. Various other cell growth chamber housings may differ in shape and size.

Those of skill in the art will recognize that the term cell growth chamber does not imply that all cells being grown or expanded in a CES are grown in the cell growth chamber. In many embodiments, adherent cells can adhere to membranes disposed in the growth chamber, or may grow within the associated tubing. Non-adherent cells (also referred to as "suspension cells") can also be grown. Cells can be grown in other areas within the first or second fluid circulation path.

For example, the ends of hollow fibers 212 can be potted to the sides of the cell growth chamber by a connective material (also referred to herein as "potting" or "potting material"). The potting can be any suitable material for binding the hollow fibers 212, provided that the flow of media and cells into the hollow fibers is not obstructed and that liquid flowing into the cell growth chamber through the IC inlet port flows only into the hollow fibers. Exemplary potting materials include, but are not limited to, polyurethane or other suitable binding or adhesive components. In various embodiments, the hollow fibers and potting may be cut through perpendicular to the central axis of the hollow fibers at each end to permit fluid flow into and out of the IC side. End caps 214 and 216 are disposed at the end of the cell growth chamber.

Fluid entering cell growth chamber 200 via inlet port 208 is in contact with the outside of hollow fibers. This portion of the hollow fiber cell growth chamber is referred to as the "extracapillary (EC) space." Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. In embodiments in which cells are grown in the IC space, the EC space is used as a medium reservoir to supply nutrients to the cells and remove the byproducts of cellular metabolism. The media may be replaced as needed. Media may also be circulated through an oxygenator to exchange gasses as needed.

In various embodiments, cells can be loaded into the hollow fibers by any of a variety of methods, including by syringe. The cells may also be introduced into the cell growth chamber from a fluid container, such as a bag, which may be fluidly associated with the cell growth chamber.

Hollow fibers are configured to allow cells to grow in the intracapillary space (i.e. inside the hollow fiber lumen) of the fibers. Hollow fibers are large enough to allow cell adhesion in the lumen without substantially impeding the flow of media through the hollow fiber lumen. In various embodiments, the inner diameter of the hollow fiber can be greater than or equal to about 10000, about 9000, about 8000, about 7000, about 6000, about 5000, about 4000, about 3000, about 2000, about 1000, about 900, about 800, about 700, about 650, about 600, about 550, about 500, about 450, about 400, about 350, about 300, about 250, about 200, about 150, or about 100 microns. Likewise, the outer diameter of the hollow fiber can be less than or equal to about 10000, about 9000, about 8000, about 7000, about 6000, about 5000, about 4000, about 3000, about 2000, about 1000, about 900, about 800, about 700, about 650, about 700, about 650, about 600, about 550, about 500, about 450, about 400, about 350, about 300, about 250, about 200, about 150, or about 100 microns. The hollow fiber wall thickness should be sufficient to allow diffusion of small molecules, in some embodiments.

Any number of hollow fibers can be used in a cell growth chamber, provided the hollow fibers can be fluidly associated with the inlet and outlet ports of the cell growth chamber. In various embodiments, the cell growth chamber can include a number of hollow fibers greater than or equal to about 1000, about 2000, about 3000, about 4000, about 5000, about 6000, about 7000, about 8000, about 9000, about 10000, about 11000 or about 12000. In other embodiments, the cell growth chamber can include a number of hollow fibers less than or equal to about 12000, about 11000, about 10000, about 9000, about 8000, about 7000, about 6000, about 5000, about 4000, about 3000, or about 2000. In other various embodiments, the length of the hollow fibers can be greater than or equal to about 100, about 200, about 300, about 400, about 500, about 600, about 700, about 800, or about 900 millimeters. In embodiments, the cell growth chamber contains approximately about 9000 hollow fibers that have an average length of about 295 mm, an average inner diameter of 215 microns, and an average outer diameter of 315 microns.

Hollow fibers can be constructed of any material capable of forming a size sufficient to form fibers capable of transporting liquid from the cell growth chamber inlet port to the cell growth chamber outlet port. In various embodiments, the hollow fibers can be constructed from plastic adherent materials capable of binding to certain types of cells, such as adherent stem cells (e.g. MSCs). In various other embodiments, hollow fibers can be treated with compounds such as fibronectin to form adherent surfaces.

In certain embodiments, the hollow fibers may be made of a semi-permeable, biocompatible polymeric material. One such polymeric material which can be used is a blend of polyamide, polyarylethersulfone and polyvinylpyrrolidone (referred to herein as "PA/PAES/PVP"). The semi-permeable membrane allows transfer of nutrients, waste and dissolved gases through the membrane between the EC space and IC space. In various embodiments, the molecular transfer characteristics of the hollow fiber membranes are chosen to minimize loss of expensive reagents necessary for cell growth such as growth factors, cytokines etc. from the hollow fiber, while allowing metabolic waste products to diffuse through the membrane into the hollow fiber lumen side to be removed.

In certain variations, one outer layer of each PA/PAES/PVP hollow fiber may be characterized by a homogenous and open pore structure with a defined surface roughness. The openings of the pores may be in the size range of about 0.5 to about 3 microns, and the number of pores on the outer surface of the fibers may be in the range of about 10,000 to about 150,000 pores per mm2. This outer layer has a thickness of about 1 to about 10 microns. The next layer in each hollow fiber may be a second layer having the form of a sponge structure and, in embodiments have a thickness of about 1 to about 15 microns. This second layer may serve as a support for the outer layer. A third layer next to the second layer may have the form of finger-like structures. This third layer provides mechanical stability and a high void volume which gives the membrane a low resistance to transporting molecules through the membrane. During use, the finger-like voids are filled with fluid and the fluid gives a lower resistance for diffusion and convection than a matrix with a sponge-filled structure having a lower void volume. This third layer may have a thickness of about 20 to about 60 microns.

In further embodiments, the hollow fiber membrane can include between about 65 to about 95% by weight of at least one hydrophobic polymer and between about 5 to about 35% by weight of at least one hydrophilic polymer. The hydrophobic polymer may be chosen from the group consisting of polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymer mixtures of any of the above polymers, such as polyethersulphone or a mix of polyarylethersulphone and polyamide. In additional embodiments, the hydrophilic polymer may be chosen from the group consisting of polyvinylpyrrolidone (PVP), polyethylene glycol (PEG), polyglycolmonoester, water soluble cellulosic derivates, polysorbate and polyethylene-polypropylene oxide copolymers.

Depending upon the type of cells to be expanded in the cell growth chamber, the polymeric fibers may be treated with a substance, such as fibronectin, to enhance cell growth and/or adherence of the cells to the membrane.

The CES can include a device configured to move or "rock" the cell growth chamber relative to other components of the cell expansion system by attaching it to a rotational and/or lateral rocking device. FIG. 1D shows one such device, in which a bioreactor 400 is rotationally connected to two rotational rocking components, and a lateral rocking component.

A first rotational rocking device component 402 rotates the bioreactor around central axis 410 of the bioreactor and laterally connects to lateral rocking device 404. Rotational rocking device component 402 is rotationally associated to bioreactor 400. The rotational rocking device then rotates bioreactor 400 around central axis 410 of the bioreactor. Rotation can occur in a clockwise or counter-clockwise direction. Bioreactor 400 can be rotated continuously in a single direction around central axis 410 in a clockwise or counter-clockwise direction. Alternatively, bioreactor 400 can rotate in alternating fashion, first clockwise, then counterclockwise around central axis 410.

The CES can also include a second rotational rocking component that rotates bioreactor 400 around rotational axis 412. Rotational axis 412 passes through the center of point of bioreactor 400 and is normal to central axis 410. Bioreactor 400 can be rotated continuously in a single direction around rotational axis 412 in a clockwise or counterclockwise direction. Alternatively, bioreactor 400 can be rotated around rotational axis 412 in an alternating fashion, first clockwise, then counterclockwise. In various embodiments, bioreactor 400 can also be rotated around rotational axis 412 and positioned in a horizontal or vertical orientation relative to gravity.

Lateral rocking component 404 is laterally associated with bioreactor 400. The plane of lateral rocking component 404 moves laterally in the −x and −y directions. The settling of cells in the bioreactor is thereby reduced movement of cell-containing media within the hollow fibers.

The rotational and/or lateral movement of the rocking device can reduce the settling of cells within the device and reduce the likelihood of cells becoming trapped within a portion of the bioreactor. The rate of cells settling in the cell growth chamber is proportional to the density difference between the cells and the suspension media according to Stoke's Law. In certain embodiments, a 180 degree rotation (fast) with a pause (having a total combined time of 30 seconds) repeated as described above keeps non-adherent red blood cells suspended. A minimum rotation of about 180 degrees is performed in some embodiments; however, one could use rotation of up to 360 degrees or greater in other embodiments. Different rocking components can be used separately, or can be combined in any combination. For example, a rocking component that rotates bioreactor 400 around central axis 410 can be combined with the rocking component that rotates bioreactor 400 around axis 412. Likewise, clockwise and counterclockwise rotation around different axes can be performed independently in any combination.

Figure 3:
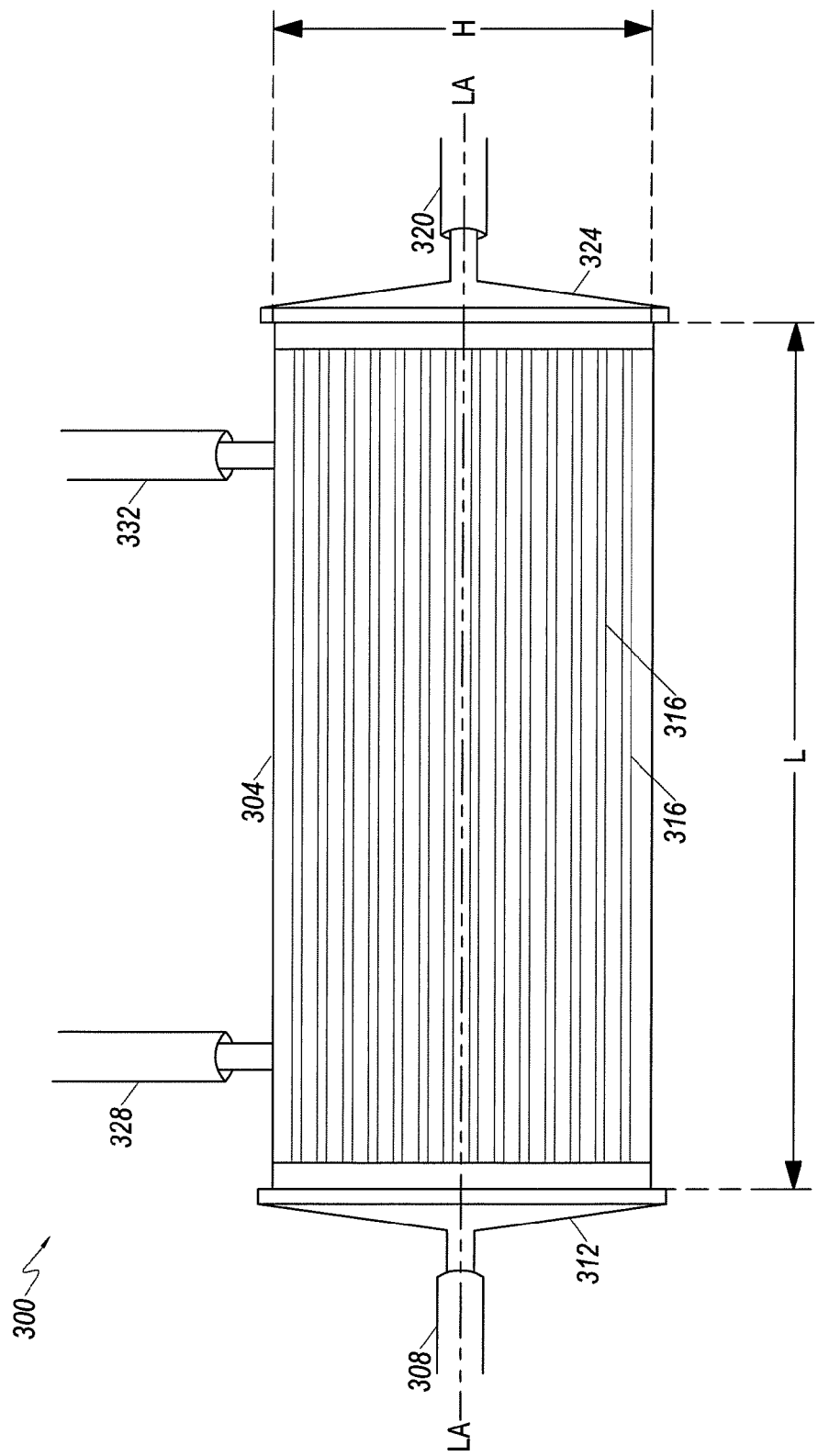
FIG. 3 is a front elevation view of an embodiment of a bioreactor showing circulation paths through the bioreactor.

With reference now to FIG. 3, an example of another cell growth chamber, bioreactor 300, is shown in front elevation view. Bioreactor 300 has a longitudinal axis LA-LA and includes bioreactor housing 304. In at least one embodiment, bioreactor housing 304 includes four openings or ports: IC inlet port 308, IC outlet port 320, EC inlet port 328, and EC outlet port 332.

Fluid in a first circulation path enters bioreactor 300 through IC inlet port 308 at a first longitudinal end 312 of the bioreactor 300, passes into and through the intracapillary side (referred to in various embodiments as the intracapillary ("IC") side or "IC space" of a hollow fiber membrane) of a plurality of hollow fibers 316, and out of bioreactor 300 through IC outlet port 320 located at a second longitudinal end 324 of the bioreactor 300. Fluid in a second circulation path flows in the bioreactor 300 through EC inlet port 328, comes in contact with the extracapillary side or outside (referred to as the "EC side" or "EC space" of the membrane) of the hollow fibers 316, and exits bioreactor 300 via EC outlet port 332. Fluid entering bioreactor via an EC inlet port 328 is in contact with the outside of the hollow fibers. Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. The media may be replaced as needed. Media may also be circulated through an oxygenator to exchange gasses as needed. Cells can be contained within the first circulation path and/or second circulation path, and can be on either the IC side and/or EC side of the membrane. By way of example and not limitation, in one embodiment, the bioreactor 300 may include about 11520 fibers that have about $215 \times 10^{-6}$ m inner diameters (ID).

Although bioreactor housing 304 is depicted as cylindrical in shape, it could have a variety of shapes, such as a rectangular cube. Bioreactor housing 304 can be made of any type of biocompatible polymeric material, including a substantially transparent material that permits an observer to see one or more of the plurality of hollow fibers 316, as well as fluid residing within the bioreactor housing 304. Various other bioreactor housings may differ in shape and size.

Figure 4:
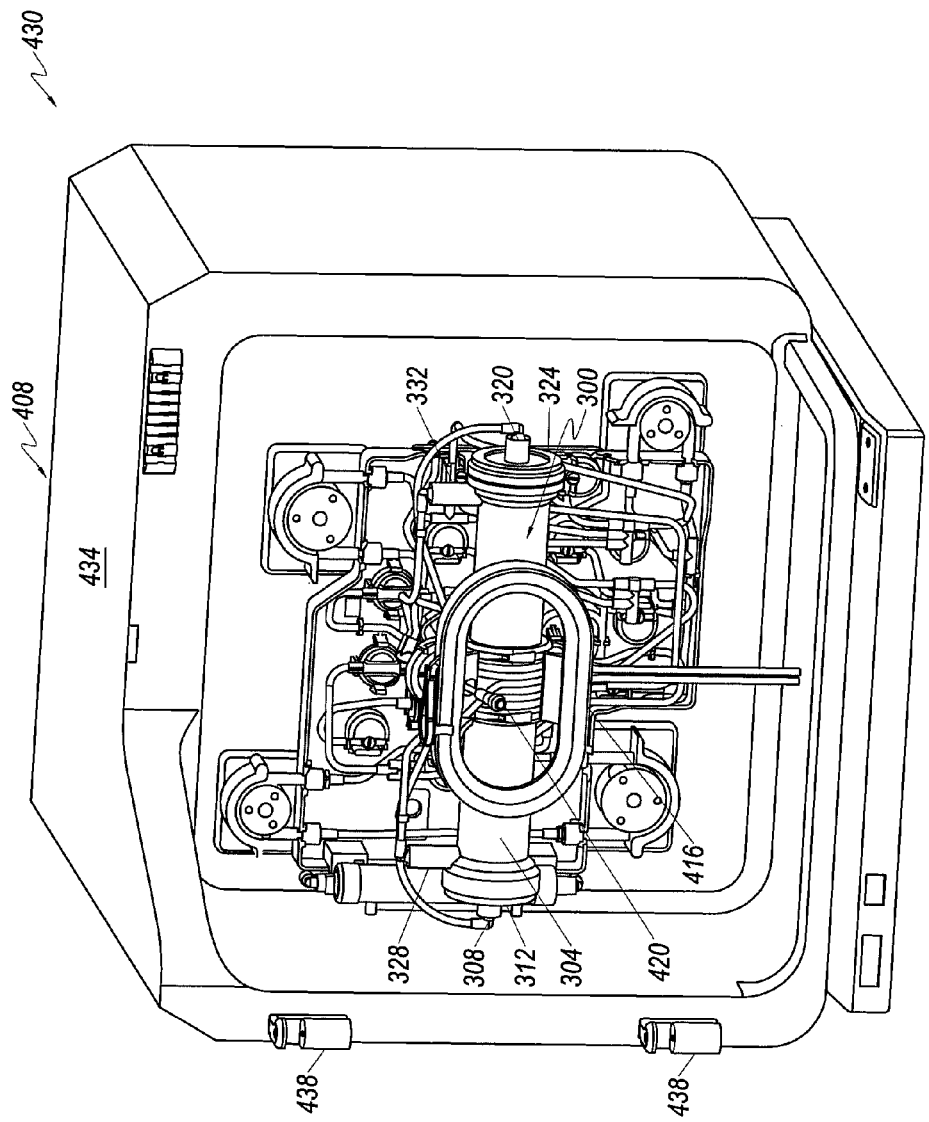
FIG. 4 is a perspective view of a portion of a cell expansion system, including a detachably attached bioreactor.

Referring now to FIG. 4, a portion of a CES 430 is shown in perspective view, and includes a back portion 434 of body 408 of the CES 430. For clarity, the front portion the body 408 is not shown; however, the front portion is attached to the back portion 434, such as by hinges 438, thereby allowing the front portion to comprise a door or hatch that can be opened to access the bioreactor 300 of the CES 430. Attached to the bioreactor 300 may be a spool 416 for tubing and a sampling port 420. The environment in the vicinity of the bioreactor 300 is temperature controlled to provide appropriate conditions for cell growth.

Figure 5:
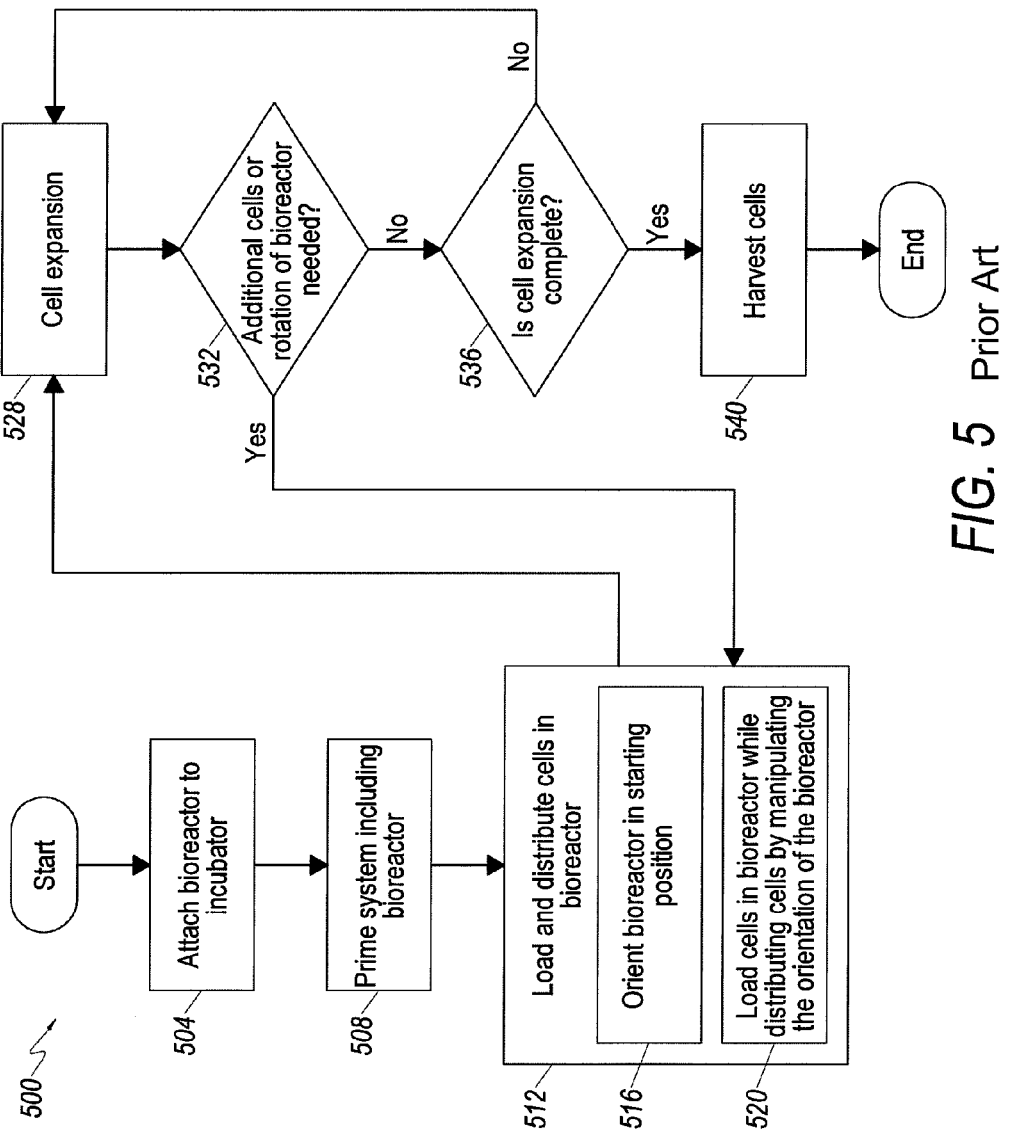
FIG. 5 is a flow chart of a method associated with loading and distributing cells in a cell expansion system.

Referring now to FIG. 5, a flow chart is shown that depicts one embodiment of a cell expansion process 500 associated with using a CES, including the steps associated with loading and distributing cells in the bioreactor 300, as further described herein. Although features of CES 430 are described as performing some of the steps of process 500, the present invention is not limited thereto. Indeed, other CES with different features, not described herein, may be utilized in some embodiments of process 500. Accordingly, reference to feature of CES 430 such as bioreactor 300 are provided for illustrative purposes only, and the process 500 is not limited to use with CES 430.

To start the cell expansion process 500, at 504 a bioreactor 300 and any associated tubing and related structures are attached to the body 408 to provide an operable CES 430. Once attached to the body 408, the bioreactor 300 and its associated tubing and related structures are primed at 508 using an appropriate priming fluid, such as saline. At 512, cells are loaded and distributed in the bioreactor 300. The loading and distributing of cells in embodiments involves a number of substeps, for example, in some embodiments step 512 additionally includes orienting the bioreactor 300 in a starting position at 516, and then loading and distributing the cells in the bioreactor 300 at 520. Following loading and distributing cells in the bioreactor 300, the cells undergo expansion at 528. That is, the cells within the bioreactor 300 are allowed to grow and/or multiply. At 532, an assessment is made as to whether additional cells need to be added to the bioreactor 300 and/or whether the bioreactor 300 needs to be rotated to distribute cells within the bioreactor 300. If additional cells need to be loaded into the bioreactor 300 and/or if cells need to be distributed in the bioreactor 300, then the cell expansion process 500 returns to step 512. If cells do not need to be added and/or the bioreactor 300 does not need to be rotated, then at 536 an assessment is made as to whether the cell expansion process 528 is complete. As used herein, the cell expansion process is determined to be complete if a sufficient number of cells and/or change in cell characteristics has been achieved. If the cell expansion process 528 is complete, the cells are harvested at 540. If cell expansion process 528 is not complete, then the cell expansion process at 528 is allowed to continue.

Figure 6:
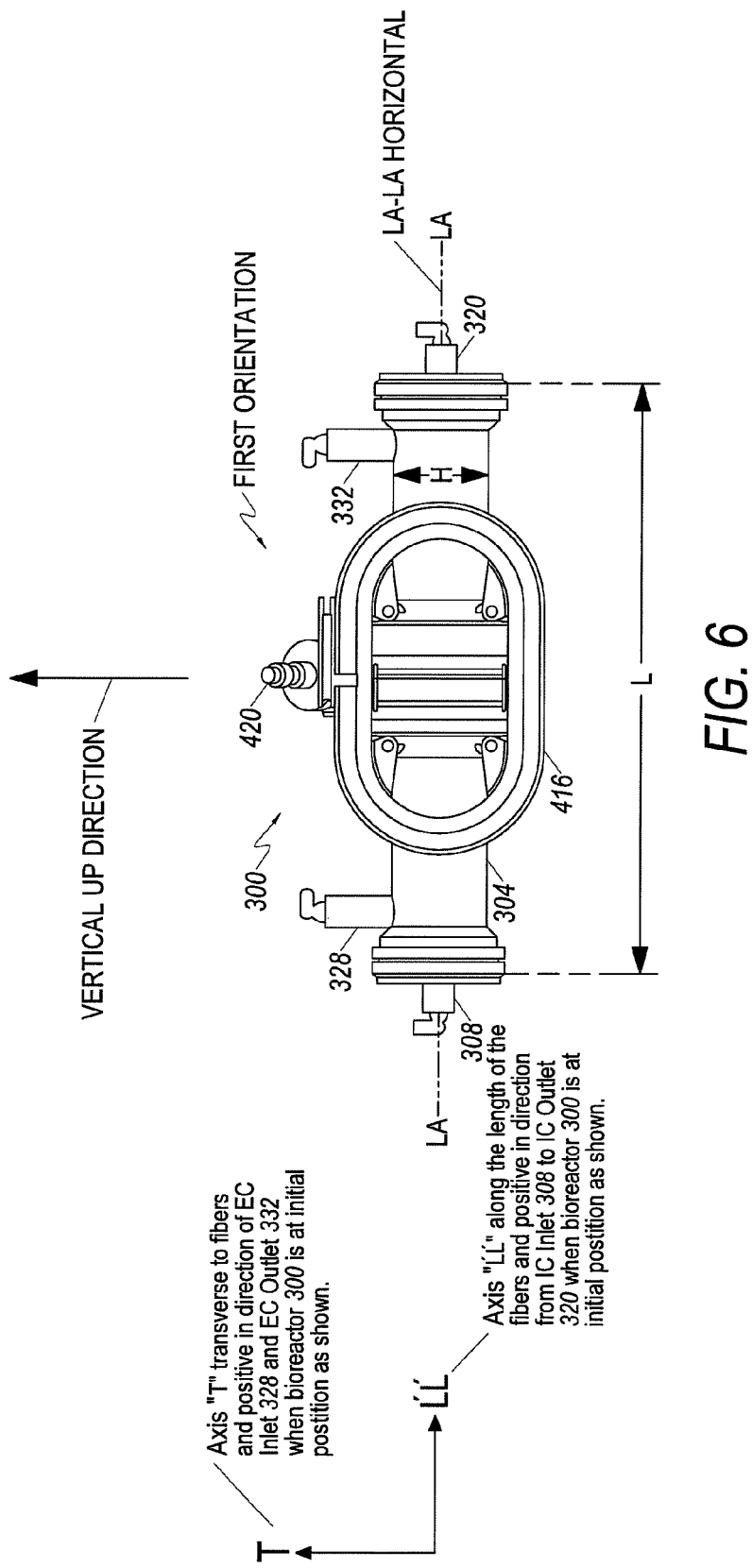
FIG. 6 is a front elevation view a bioreactor in a first orientation.

With further reference to the flow chart of FIG. 5, additional detail is now provided regarding loading and distributing cells in the bioreactor, as shown at 512. More particularly, at 516, the bioreactor 300 is oriented in its starting position. As best seen in FIG. 6, in at least one embodiment the bioreactor 300 is positioned horizontally to initiate loading and distributing cells in the bioreactor 300. That is, after the bioreactor 300 is primed at 508, at 516 the bioreactor 300 is oriented with its longitudinal axis LA-LA in a starting position, such as a substantially horizontal position. Thereafter, at 520 a plurality of cells is loaded into the bioreactor 300 while the bioreactor 300 is rotated (as described below) in a particular sequence to facilitate distribution of the cells through the bioreactor 300.

In at least one embodiment, cells may be loaded into the IC side of the bioreactor 300 (or into the hollow fibers 316 of the bioreactor 300) by causing flow of a media carrying the cells to pass from the IC inlet 308 to the EC outlet 332. In addition, cells may be loaded into the EC side of the bioreactor 300 (or to the exterior of the hollow fibers 316 of the bioreactor 300) by causing flow of a media carrying the cells to pass from the EC inlet 328 to the IC outlet 320.

To assist with determining the desired movements of the bioreactor 300 to facilitate improved distribution of cells within the bioreactor 300, a series of calculations may be performed, for one embodiment, to calculate a basis for positioning the bioreactor 300. More particularly, by rotating the bioreactor 300, the influence of the acceleration due to gravity on a given cell (e.g., bone marrow cell) within the bioreactor 300 can be affected relative to the geometry of the bioreactor 300. To achieve a net impulse of zero on the cell, calculation of the impulse ("I") may be performed to determine the change during rotation and counteract the impulse with the appropriate pause time at 0° and 270°.

To start, initial consideration may be given to the acceleration experienced by a cell within the bioreactor 300. As a premise of embodiments of the present invention, it may be desirable to counteract the acceleration due to gravity ("g") on a given cell in the bioreactor 300 associated with distributing cells in the bioreactor 300. Accordingly, a rotation sequence for the bioreactor 300 is sought to achieve a net gravitational influence on a given cell of zero associated with loading and distributing cells in the bioreactor 300. Table 1 below provides a summary of gravitational acceleration influences along two axes, namely, the T and $\overline{LL}$ axes as shown in FIG. 6, associated with the bioreactor 300.

TABLE 1

Summary Table Of Acceleration Directions

| Bioreactor Position | $a_T$ | $a_{\overline{LL}}$ |
|---|---|---|
| At 0° | − (g is purely along T axis) | 0 |
| While Rotating 0° to 90° | − (a component of g is along T axis) | − (a component of g is along $\overline{LL}$ axis) |
| While Rotating 90° to 180° | + (a component of g is along T axis) | − (a component of g is along $\overline{LL}$ axis) |
| While Rotating 180° to 270° | + (a component of g is along T axis) | + (a component of g is along $\overline{LL}$ axis) |
| Paused at 270° | 0 | + (g is purely along $\overline{LL}$ axis) |
| While Rotating 270° to 180° | + (a component of g is along T axis) | + (a component of g is along $\overline{LL}$ axis) |
| While Rotating 180° to 90° | + (a component of g is along T axis) | − (a component of g is along $\overline{LL}$ axis) |
| While Rotating 90° to 0° | − (a component of g is along T axis) | − (a component of g is along $\overline{LL}$ axis) |

Figure 7:
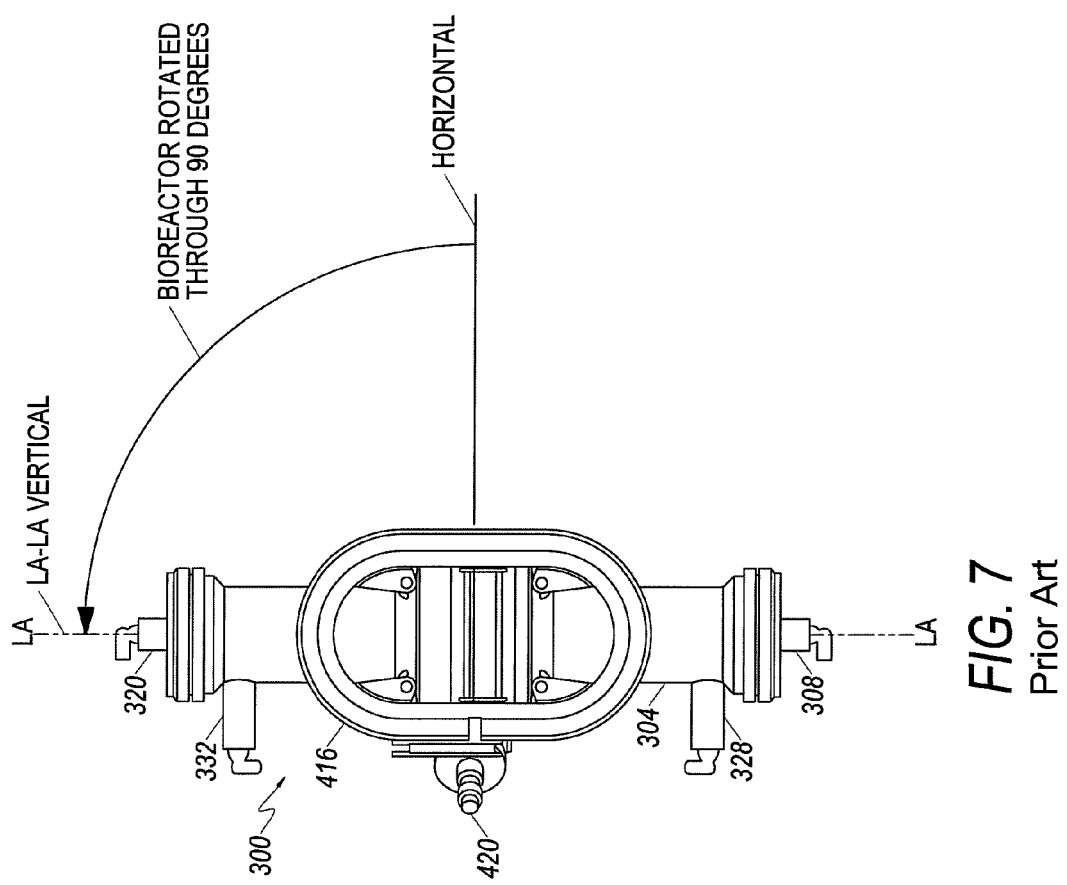
FIG. 7 is a front elevation view of the bioreactor of FIG. 6, wherein the bioreactor is shown rotated through 90° of rotation.
Figure 8:
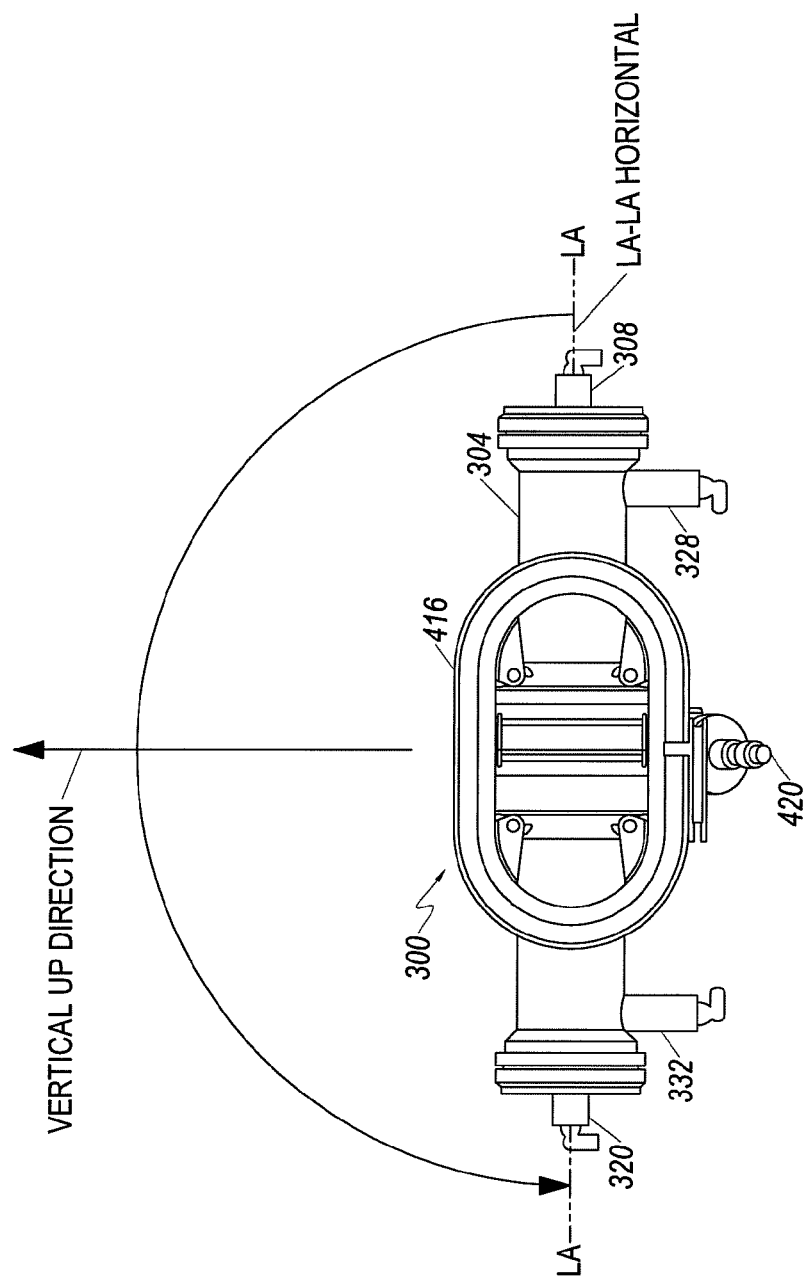
FIG. 8 is a front elevation view of the bioreactor of FIG. 6, wherein the bioreactor is shown rotated through 180° of rotation.
Figure 9:
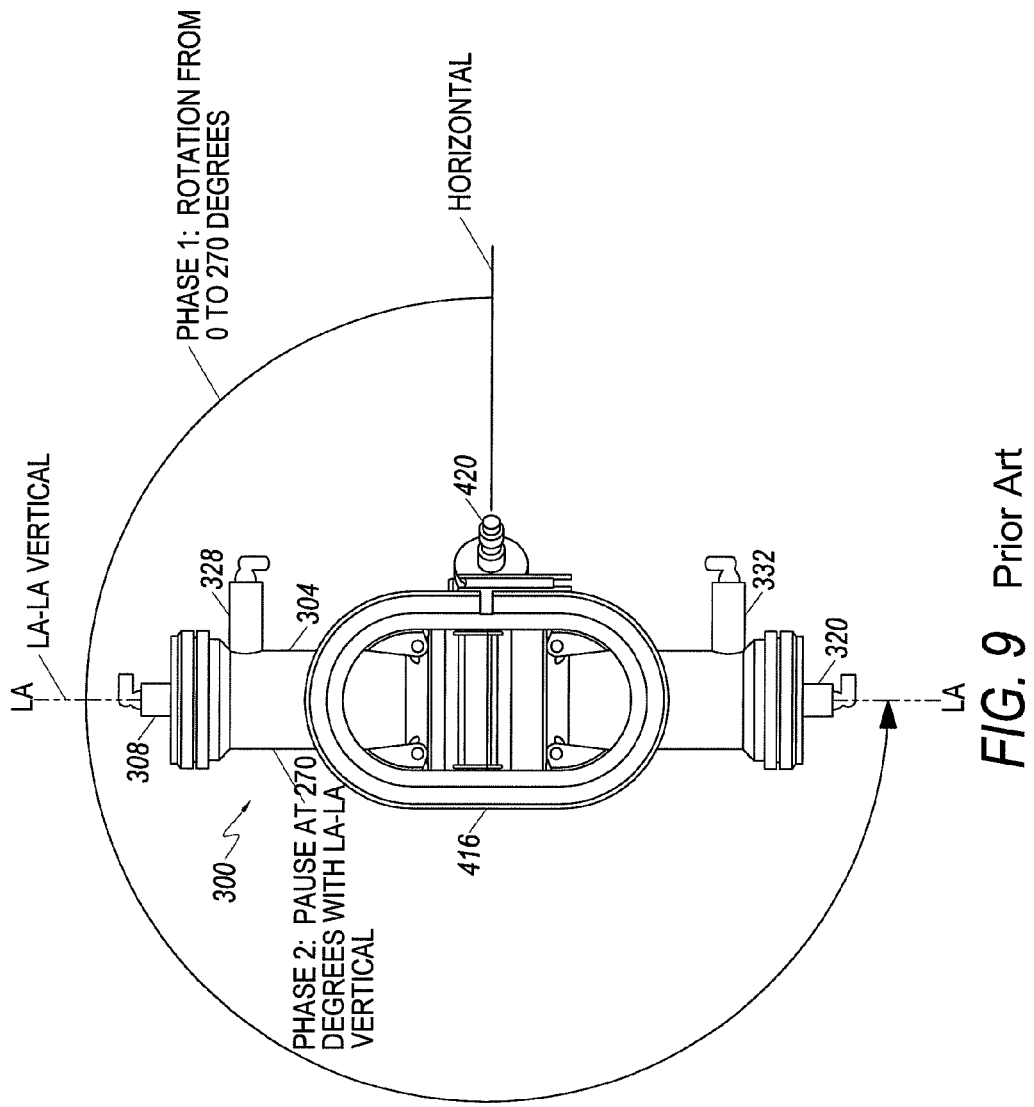
FIG. 9 is a front elevation view of the bioreactor of FIG. 6, wherein the bioreactor is shown rotated through 270° of rotation and to a second position.

For Table 1, a positive sign "+" indicates acceleration in the positive direction for the subject axis when the bioreactor is at the position or while rotating as shown in column 1; a negative sign "−" indicates acceleration in the negative direction for the subject axis when the bioreactor is at the position or while rotating as shown in column 1; and zero "0" indicates substantially no acceleration for the subject axis when the bioreactor is at the position as shown in column 1. Zero degrees (0°) is defined as the orientation of the bioreactor 300 when the longitudinal axis LA-LA is oriented horizontally with the EC inlet 328 and EC outlet 332 oriented upwards (as shown in FIG. 6); 90° is defined as vertical with the EC inlet 328 and EC outlet 332 oriented to the left (as shown in FIG. 7); 180° is defined as the longitudinal axis LA-LA oriented horizontally with the EC inlet 328 and EC outlet 332 oriented downwards (as shown in FIG. 8); and 270° is defined as vertical with the EC inlet 328 and EC outlet 332 oriented to the right (as shown in FIG. 9).

A method of distributing cells in a bioreactor 300 includes manipulating the orientation of the bioreactor 300, such that a net impulse due to gravity acting on cells loaded into the bioreactor 300 is substantially zero. In accordance with at least one embodiment, the manipulation of the bioreactor comprises both rotating the bioreactor 300 and thereafter holding the bioreactor stationary for set periods of time. In accordance with at least one embodiment, the time for holding the bioreactor 300 stationary $t_p$ is approximately equal to the quantity $2\omega^{-1}$, wherein the angular velocity $\omega$ (rad/sec) is substantially constant for the periods when the bioreactor 300 is undergoing rotation. As those skilled in the art will appreciate, different angular velocities and pause times can be used.

Figure 10:
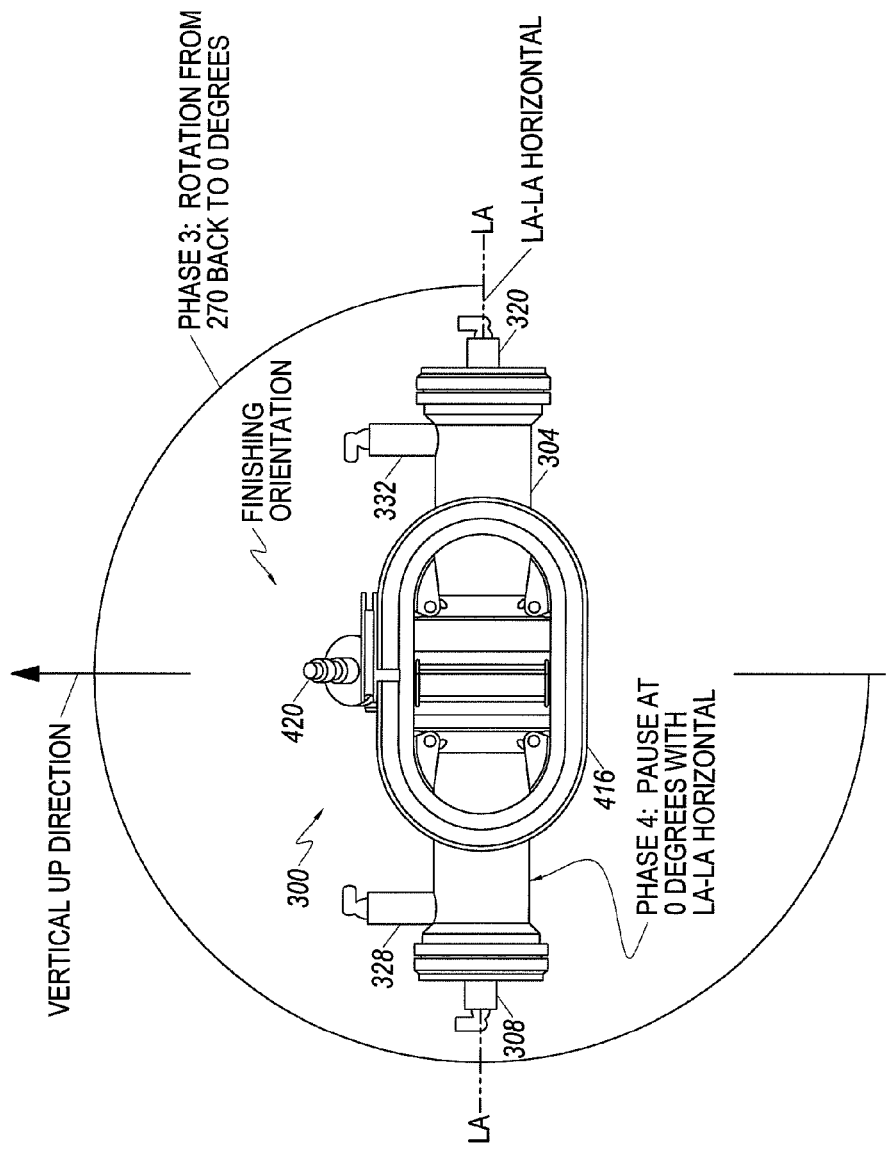
FIG. 10 is a front elevation view of the bioreactor of FIG. 6, wherein the bioreactor is shown rotated back to the initial starting position.

Referring again to FIG. 6, and in accordance with at least one embodiment, the orientation of the bioreactor 300 at the initial starting position is shown. Here, the longitudinal axis LA-LA of the bioreactor is substantially horizontal. While loading cells into the bioreactor 300, a sequence of manipulations is undertaken to mitigate the influence of gravity on the cells loaded into the bioreactor 300. More particularly, in embodiments, the bioreactor 300 is rotated though approximately 270° at a first angular velocity $\omega$. FIG. 7 illustrates the bioreactor 300 rotated through 90°. Continuing, FIG. 8 illustrates the bioreactor 300 having been rotated through 180°. Finally, FIG. 9 illustrates the bioreactor oriented at a second orientation, where the bioreactor 300 is held still for a period of time to allow the full influence of gravity to act in the positive direction of the LL axis. After the appropriate period of time for pausing the bioreactor 300, the bioreactor 300 is then rotated back to its original or initial starting position, as shown in FIG. 10.

As those skilled in the art will appreciate, more than one rotational direction is possible. In addition, more than one initial starting position is also possible provided a balancing of the influence of gravity on the cells loaded into the bioreactor 300 is achieved. Accordingly, the calculations, examples and discussion herein provide one or more possible configurations for manipulating the bioreactor 300 to reduce, minimize or eliminate the influence of gravity on cells and improve distribution of cells within the bioreactor. However, to the extent that other embodiments and variations are encompassed by the present disclosure, the calculations, description and figures are to be considered exemplary and non-limiting.

In accordance with at least one embodiment, the influence of gravity on cell distribution in the bioreactor 300 is controlled by the angular velocity applied to the bioreactor 300. More particularly, the rotational or angular velocity $\omega$ (rad/sec) is used to balance the net impulse due to gravity experienced by cells within the bioreactor 300.

In accordance with at least one embodiment, a method of distributing cells within a bioreactor 300 having a longitudinal axis LA-LA includes: initiating the loading and distributing of cells into the bioreactor 300 when the longitudinal axis LA-LA is substantially horizontal or angled at about 45° relative to horizontal; rotating the bioreactor 300 through a total of approximately 540° of angular displacement; and holding the bioreactor 300 still at a plurality of orientations. In at least one embodiment, the angular velocity of rotation is substantially the same for those intervals of time wherein the bioreactor is rotating. In at least one embodiment, the angular velocity of rotation of the bioreactor 300 is changed from a first angular velocity $\omega_1$ to a second angular velocity $\omega_2$ for portions of the time the bioreactor 300 is undergoing rotation.

Figure 11:
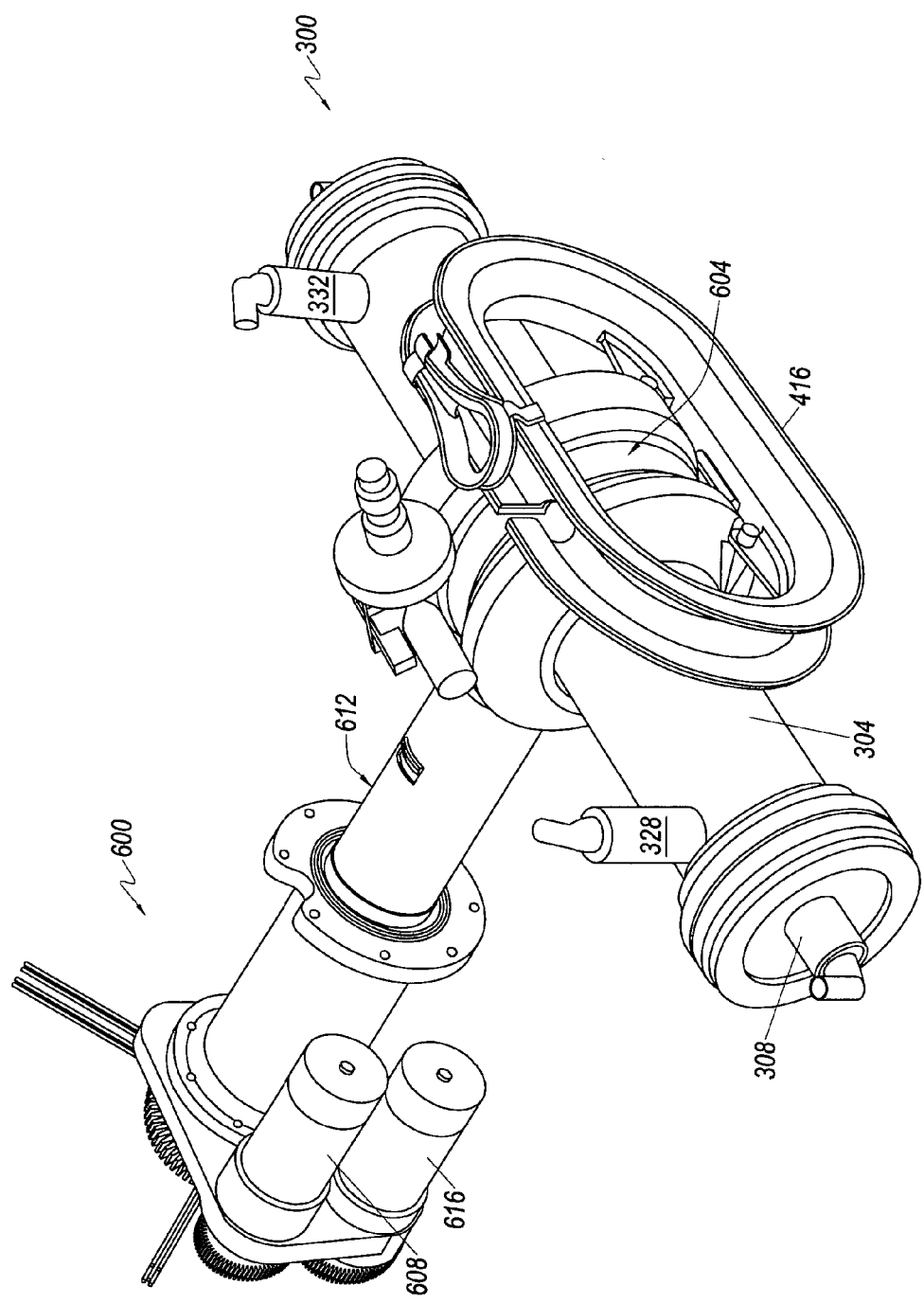
FIG. 11 is a perspective view of a bioreactor connected to a shaft assembly of a CES.
Figure 12:
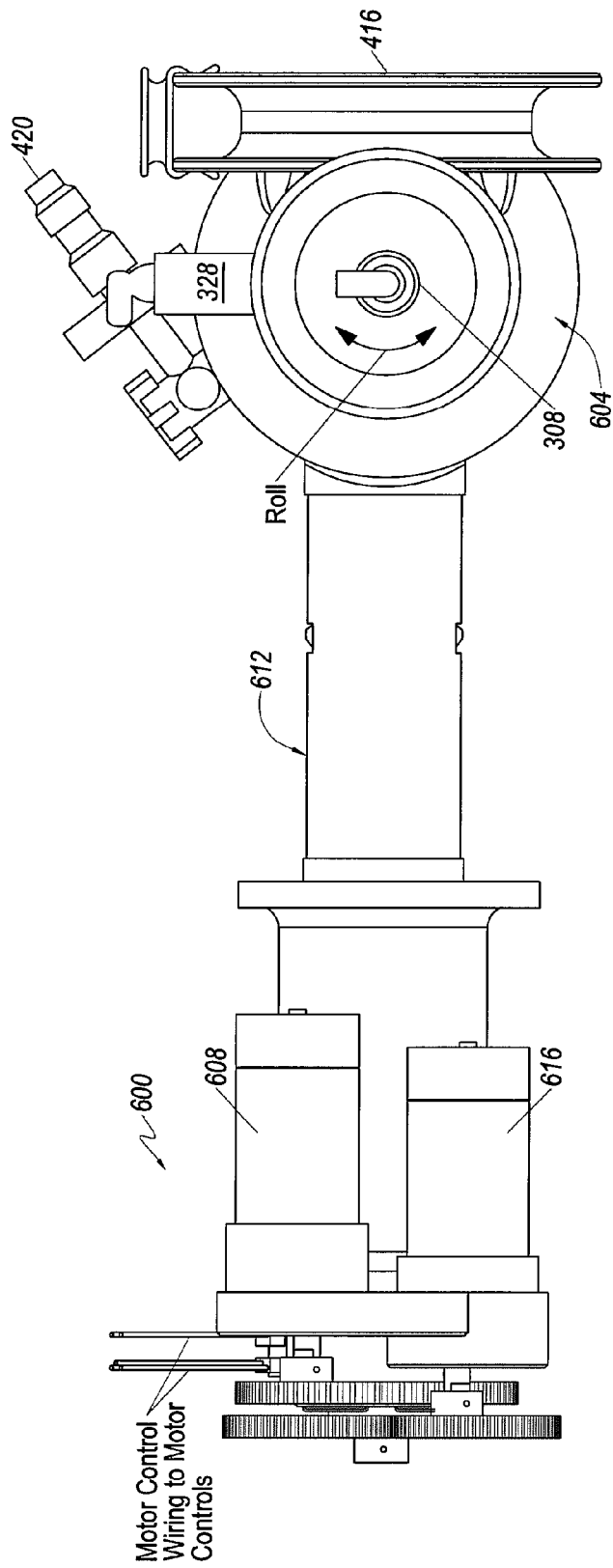
FIG. 12 is a side elevation view of the structures shown in FIG. 11.
Figure 13:
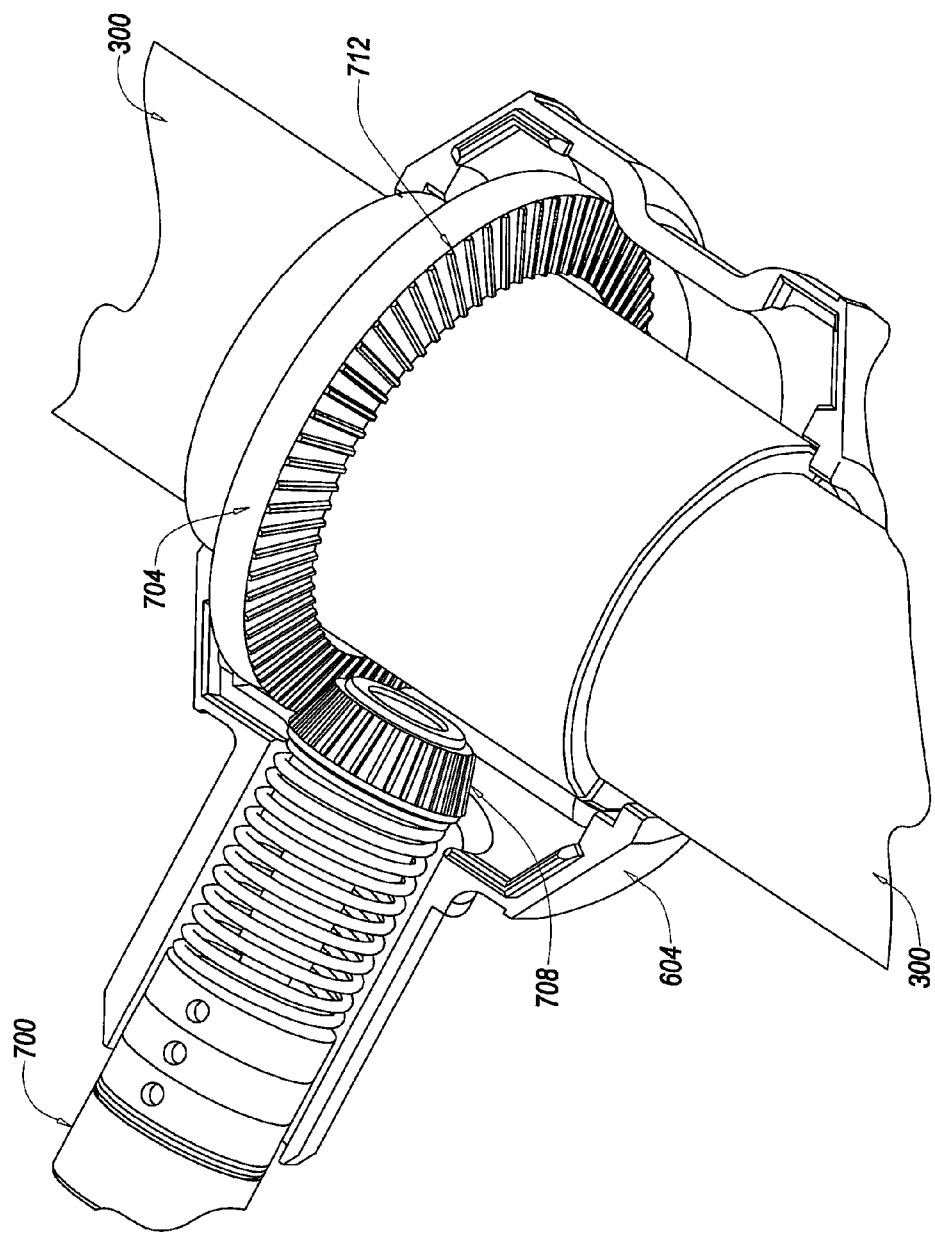
FIG. 13 is a detail perspective view of a fitting used to rotate a bioreactor around its longitudinal axis.

Referring now to FIGS. 11 and 12, different views of the bioreactor 300 are shown with the bioreactor 300 interconnected to a shaft assembly 600 by a chamber coupling 604. Motor 608 serves to rotate the outer shaft 612 around a rotation axis oriented through the shaft 612 and substantially perpendicular to the longitudinal axis of the bioreactor 300, thereby rotating the bioreactor 300 in a pitch mode as illustrated in FIGS. 7-10. Motor 616 serves to rotate an inner shaft (see FIG. 13) located within the outer shaft 612 to cause a roll fitting within the chamber coupling 604 to rotate the bioreactor 300 around its longitudinal axis LA-LA. As best seen in FIG. 13, an inner shaft 700 includes structure for engaging a roll collar 704 residing within the chamber coupling 604. The inner shaft member 700 includes a beveled pinion 708 residing at the very distal end of the inner shaft member 700, and the beveled pinion 708 contacts a sloped surface 712 of the roll collar 704 such that when the inner shaft member 700 is rotated, the roll collar 704 rotates, thereby causing the cell growth chamber 300 to rotate about its longitudinal axis LA-LA.

Figure 14:
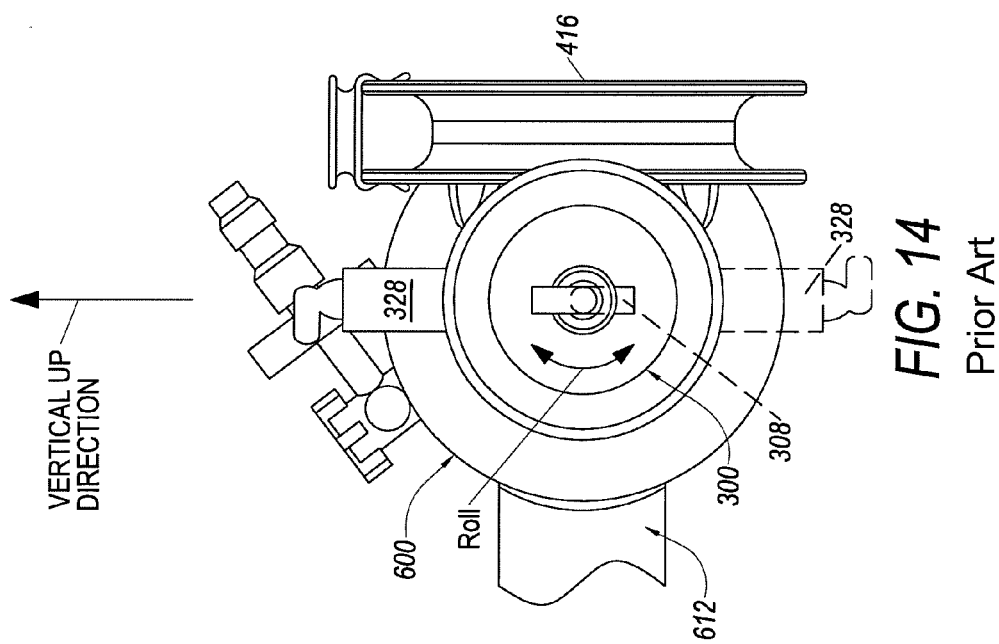
FIG. 14 is a side elevation view of a bioreactor illustrating rotation in roll.

With reference now to FIG. 14, an example of rotating the cell growth chamber in the roll mode is illustrated. In FIG. 14, a side elevation view of the cell growth chamber 300 is shown, wherein in a first roll position (shown with solid lines), the EC inlet port 328 is oriented vertically upwards. In a second roll position (shown with dashed lines), the EC inlet port 328 is oriented downwards. It is to be understood that the roll of the cell growth chamber 300 can be selectively controlled such that the cell growth chamber 300 can be rotated at any angle around its longitudinal axis. Periodic rotation of the cell growth chamber 300 in roll assists in preventing colonies of cells from settling during the cell loading and distribution process at step 512 depicted in the flow chart shown in FIG. 5.

In at least one embodiment, cells are loaded and distributed throughout the bioreactor 300 during a loading and distribution step that operates for greater than about 2 minutes of time. In at least one embodiment the loading and distribution step may operate for several minutes. During the loading and distribution step the bioreactor 300 undergoes a plurality of rotational sequences that are undertaken consecutively from the time loading of the cells is commenced until such time as substantially all of the cells have been loaded into the bioreactor 300 and its associated tubing.

In at least one embodiment, a bioreactor 300 is loaded with a plurality of cells while undergoing rotation such that a net impulse due to gravity acting on the plurality of cells is reduced relative to a net impulse due to gravity acting on the plurality of cells if the bioreactor 300 was not undergoing rotation. That is, the method comprises manipulating an orientation of the bioreactor such that an actual net impulse due to gravity acting on the plurality cells in the bioreactor is reduced relative to an avoided net impulse due to gravity acting on the plurality cells if the bioreactor was held in a stationary position.

In at least one embodiment, the bioreactor 300 is rotated through at least 180° of rotation to reduce the net impulse of gravity acting on the plurality of cells.

In at least one embodiment, the bioreactor 300 is rotated in a pitch mode to reduce the net impulse due to gravity acting on the plurality of cells, wherein an axis of rotation is oriented transversely to a longitudinal axis LA-LA of the bioreactor 300. In at least one embodiment, the bioreactor 300 is rotated in a roll mode to reduce the net impulse due to gravity acting on the plurality of cells, wherein an axis of rotation is oriented substantially parallel to a longitudinal axis LA-LA of the bioreactor 300. Here, the axis of rotation that is substantially parallel to the longitudinal axis LA-LA may be coincident with the longitudinal axis LA-LA.

In at least one embodiment, harvesting of cells from the bioreactor 300 is performed by manipulating the orientation of the bioreactor 300 as described herein. That is, the bioreactor 300 is rotated to reduce a net impulse due to gravity acting on the cells during the harvesting procedure. Such manipulation of the bioreactor during cell harvesting improves the collection efficiency of cells. In addition, such manipulation of the bioreactor during cell harvesting also improves the number of cells collected because the influence of gravity is overcome as the cells are washed from the bioreactor 300.

In at least one embodiment wherein cells are grown in a suspension and not adhered to the walls of hollow fibers in the bioreactor, the bioreactor can be continuously manipulated to reduce the influence due to gravity on cells residing with the bioreactor.

Figure 22:
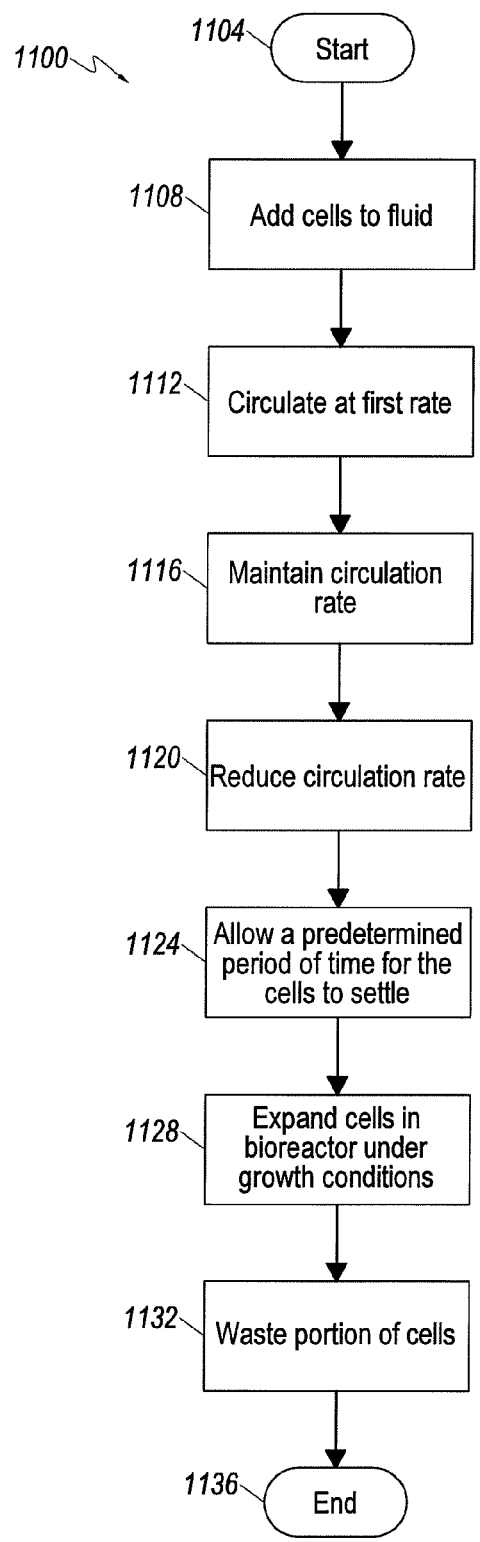
FIG. 22 is a flow chart of a method associated with loading and distributing cells in a cell expansion system according to an embodiment.

Cells can be added to the CES by a number of methods. As noted above, with respect to FIG. 5, loading and distributing cells may involve a number of steps or substeps. FIG. 22 illustrates a process 1100 for expanding/growing cells that includes a number of steps for loading and distributing cells in a cell growth chamber or bioreactor. The steps below may be described with respect to features of a system, but the present invention is not limited thereto. In other embodiments, the steps may be performed by other components of CES. Accordingly, the steps of process 1100 are not limited to being performed by any particular structure.

Process 1100 being at 1104. At step 1108, cells are added to fluid circulating in a cell growth chamber. In one embodiment, the cells are loaded into an intracapillary ("IC") space loop of a bioreactor (e.g., bioreactor 300) and uniformly suspended using circulation. Fluid in the IC loop may be circulating while the cells are added into the IC space loop. At step 1112 the cells are circulated though a cell growth chamber at a first rate. The circulation of the fluid may be performed using a circulation pump.

At step 1116, the circulation rate is maintained for a predetermined period of time. In some embodiments, the circulation pump may be circulating the fluid in the IC loop at one rate when the cells are introduced (e.g., step 1108), and then circulate the fluid at a second higher rate after the cells are introduced. In these embodiments, step 1116 involves maintaining the circulation at the second higher rate.

Once cells are uniformly suspended, step 1120 is performed to reduce the circulation rate. Step 1120 may involve reducing the rate of a circulation pump or completely stopping the pump. In any case, the rate at which the fluid is circulating is reduced at step 1120. At step 1124, the cells are then allowed to settle. As will be appreciated, the cells are approximately uniformly distributed throughout the system, e.g., CES 10, 900, 800. At step 1124, cells located within the bioreactor will settle in the bioreactor and cells outside of the bioreactor will settle outside of the bioreactor.

At step 1128, cells that settled in the bioreactor at step 1124, are expanded in the bioreactor. Step 1128 may involve circulating fluid, such as media and other nutrients to the bioreactor to promote the cell growth. The cells that settled outside of the bioreactor will be wasted, as they will not be in the bioreactor under the conditions that promote their growth. Accordingly, at step 1132, the cells that settled outside of the bioreactor at step 1124 are wasted. By the term "wasted" it is meant that the cells are not subjected to conditions that are optimized to promote growth of the cells, as occurs in the bioreactor. Therefore, the wasted cells are not expanded in the bioreactor, and in some embodiments the wasted cells die and/or are washed away in fluid circulating in a CES. The wasted cells may in some embodiments expand or grow in other parts of a CES, and in some embodiments they may even be harvested, but they will not be subjected to the same conditions, optimized for their growth, as cells in the bioreactor. The process ends at 1136.

In some embodiments process 1100 is performed in a system where the volume in the bioreactor is from about 65% to about 70%, such as about 69%, of the volume containing cells, e.g., the volume of the IC loop. When the cells are settled at step 1124, from about 30% to about 35%, such as about 31%, of the cells (located in the volume outside of the IC loop) will be wasted.

The cells that are distributed in a bioreactor, according to embodiments of process 1100, are less influenced by the distribution of the cells since they are generally evenly distributed in the bioreactor, and the loss of wasted cells does not result in reduced numbers of expanded cells compared to conventional methods of loading cells.

In conventional methods of loading cells in the bioreactor, steps were performed to attempt to push cells that settled in the volume of the IC loop, which is not within the bioreactor, into the volume within the bioreactor. The circulation of liquid in the IC loop was changed so that cells were chased from the input line and the output line into the bioreactor by flowing fluid from the lines into both the input and output ends of the bioreactor. Without being bound by theory, it is believed that this increased the amount of cells in the bioreactor, but did not provide an even distribution of cells. The even distribution of cells, as provided with the method described above (process 1100), creates a more favorable environment for cell expansion and makes up for the smaller initial amount of cells distributed in the bioreactor compared to the previous methods.

It is noted that the method described above is provided merely for illustrative purposes. Other variations are within the scope of the present invention. For example, the IC loop may be such that the percentage of cells that are deposited in the bioreactor is equal to or greater than about 50, about 55, about 60, about 65, about 70, about 75, about 80, about 85, about 90, or about 95 percent of the cells introduced into the IC loop of a CES. In some embodiments, the IC loop of a CES may be such that the amount of cells that are deposited in the bioreactor is less than or equal to about 95, about 90, about 85, about 80, about 75, about 70, about 65, or about 60 percent of the cells introduced into the IC loop of a CES.

As noted above, in some embodiments the circulation rate of the circulation pump can change during various steps of process 1100. For example, the circulation rate may be at a first rate when the cells are introduced into the IC loop, step 1108. The rate may then be increased after the cells are introduced into the IC loop. In other embodiments, the circulation pump may be off, or at a low circulation rate, when the cells are introduced into the IC loop and then turned on, or increased, after the cells are introduced. In embodiments, the circulation rates in the IC loop, during various steps of the methods, may be greater than or equal to about 25 ml/min, about 50 ml/min, about 75 ml/min, about 100 ml/min, about 125 ml/min, about 130 ml/min, about 135 ml/min, about 140 ml/min, about 145 ml/min, or about 150 ml/min. In embodiments, the circulation rates in the IC loop, during various steps of the methods, may be less than or equal to about 400 ml/min, about 375 ml/min, about 350 ml/min, about 325 ml/min, about 300 ml/min, 275 ml/min, about 250 ml/min, about 225 ml/min, about 200 ml/min, about 175 ml/min, about 170 ml/min, about 165 ml/min, about 160 ml/min, about 155 ml/min, 150 ml/min, 145 ml/min, or 140 ml/min.

In some embodiments, in addition to circulation of the IC loop to evenly distribute the cells in the IC loop volume, the bioreactor may also be rotated to further evenly suspend the cells before the circulation pump is turned off, or is set at a low circulation rate. The rotation of the bioreactor may be performed as described above with respect to FIGS. 3-14, before, during, and/or after cells are introduced into the IC loop volume.

EXAMPLES

In this example, hMSC cells are expanded in a bioreactor using a loading and distribution method similar to the methods described above.

Day 0-5 Expansion of the cells: 13.6 M to 177 M; CV=10%; dT=32.7 hrs

Day 5-6 Expansion: 177 M to 296 M; CV=10%; dT=32.4 hrs

Day 6-7 Expansion: 296 M to 408 M; CV=1%; dT=51.7 hrs

Cells in flask culture at approximately 80% confluence at Day 7, harvest 20,160 cells/cm2. In a CES, 19,429 cells/cm2 are harvested at Day 7. This may be an indication of approximately 80% confluence in the bioreactor.

The approximately 80% confluent indicator, the elongation of the cell doubling time from Day 6 to Day 7 (32 hrs to 51 hrs), and decrease in CV % all suggest the cells are being slowed by cell-cell interactions and the capacity of the bioreactor is approaching the maximum for this particular cell population.

Figure 15:
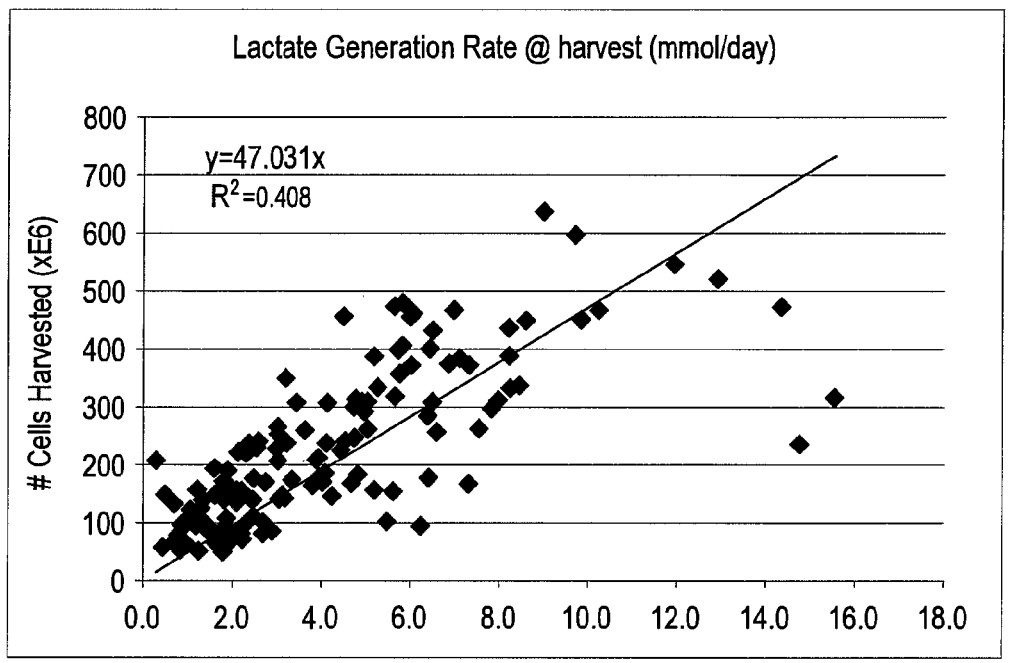
FIG. 15 is a graph showing expanded cells harvested after being loaded and distributed using previous methods.
Figure 16:
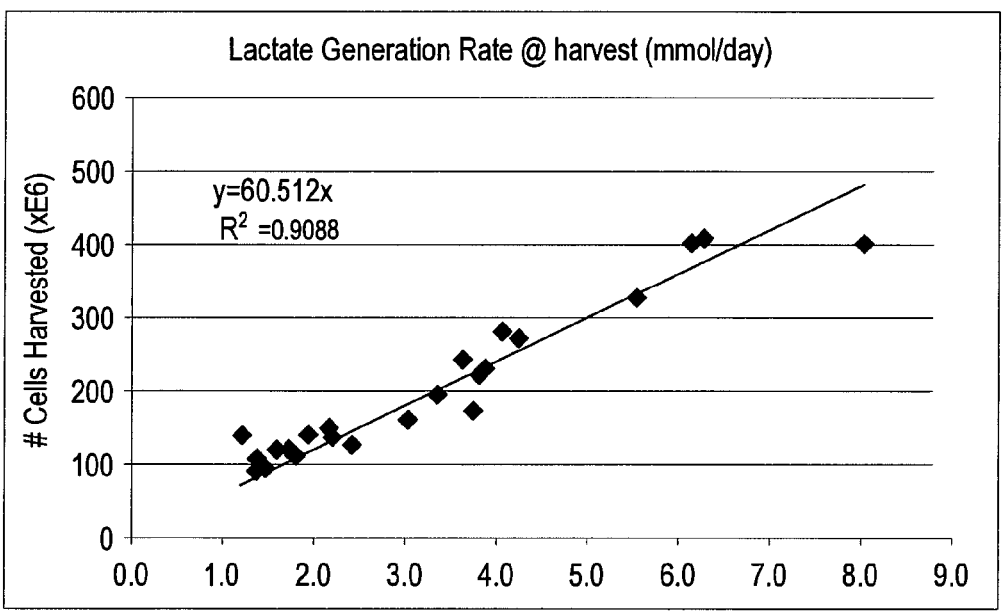
FIG. 16 is a graph showing expanded cells harvested after being loaded and distributed using methods consistent with embodiments of the present invention.

FIG. 15 illustrates cell harvest numbers as a function of lactate generation rate for cells that are loaded and distributed using conventional methods. FIG. 16 illustrates cell harvest numbers as a function of lactate generation rate for cells that are loaded and distributed using a method consistent with the methods described above, i.e., embodiments of the present invention such as embodiment of process 1100. Comparing FIG. 15 to FIG. 16 shows that harvest numbers are more predictable (as shown with FIG. 16) when rates are associated with cell populations that are expanding uniformly (i.e. well distributed during seeding).

Figure 17:
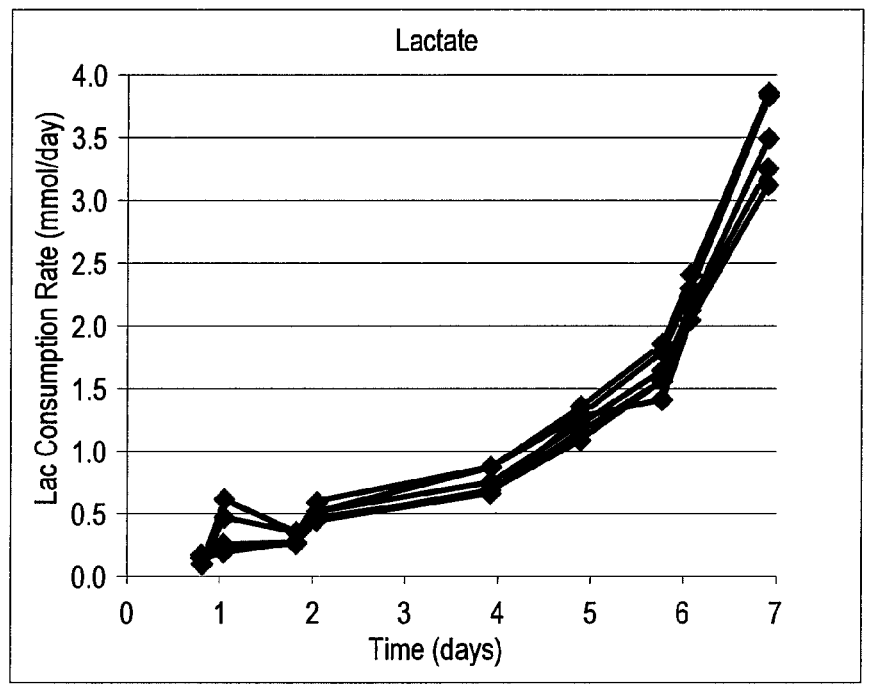
FIG. 17 is a graph showing lactate generation during expansion for cells that have been loaded and distributed using methods consistent with embodiments of the present invention.
Figure 18:
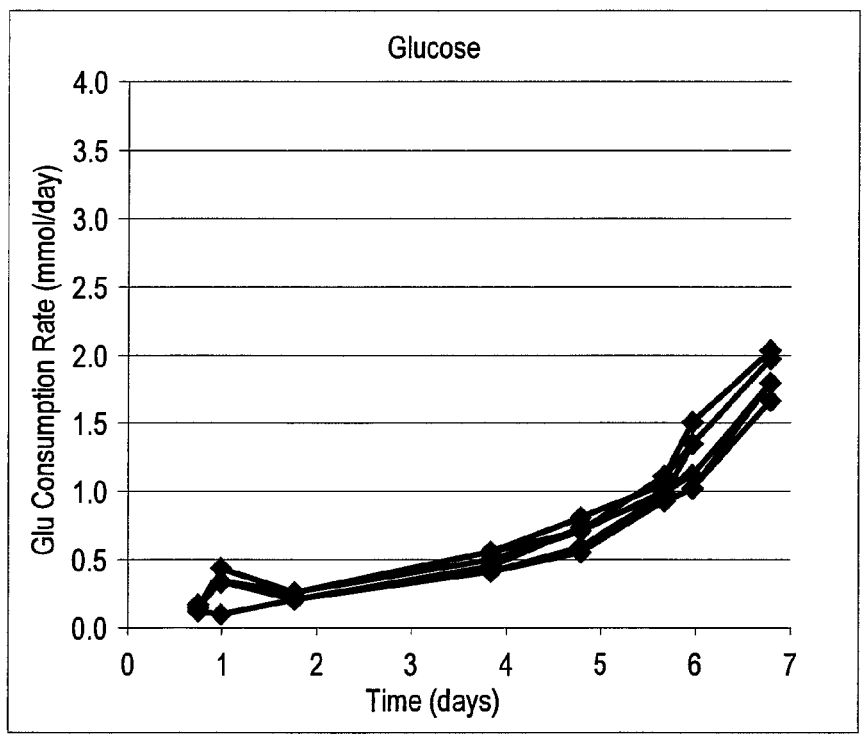
FIG. 18 is a graph showing glucose consumption during expansion for cells that have been loaded and distributed using methods consistent with embodiments of the present invention.

FIGS. 17 and 18 illustrate data for cells loaded and distributed consistent with methods described above, i.e., embodiments of the present invention such as process 1100. FIG. 17 illustrates lactate generation and FIG. 18 illustrates glucose consumption. FIGS. 17 and 18 illustrate high run-to-run consistency. FIGS. 17 and 18 show doubling time: Flask CV %=9.4, Embodiment of Present Invention CV %=2.4; and cells/cm2 at harvest: Flask CV %=28.0, Embodiment of Present Invention CV %=10.2. Cell population exponential growth is a sign of even cell distribution; particularly after 7 days of expansion.

Figure 19:
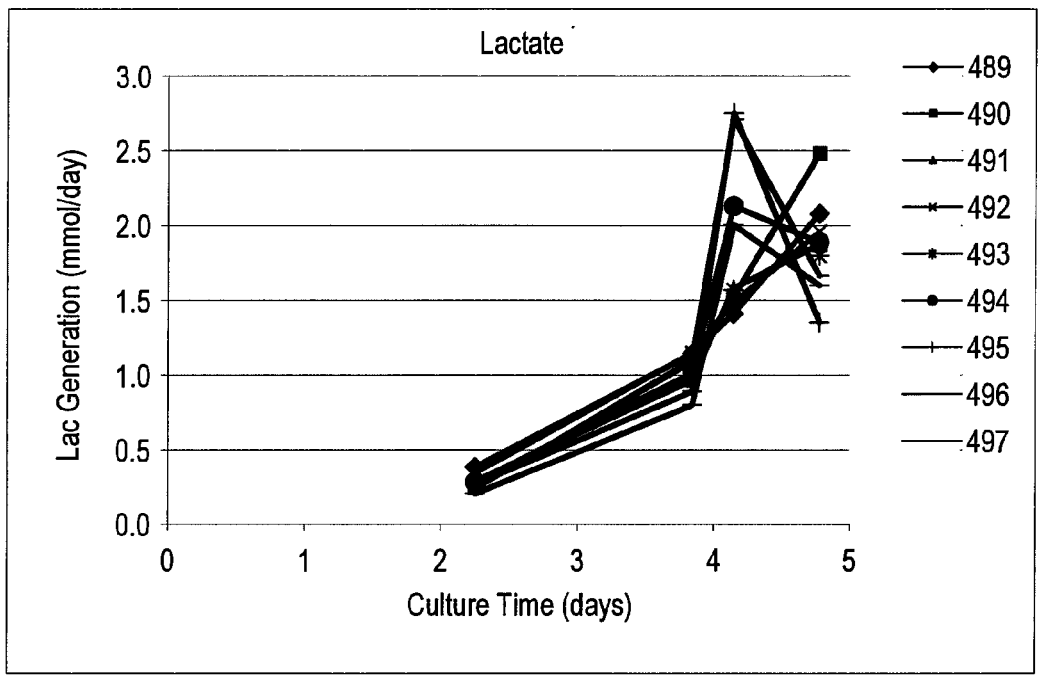
FIG. 19 is a graph showing lactate generation during expansion for cells after being loaded and distributed using previous methods.
Figure 20:
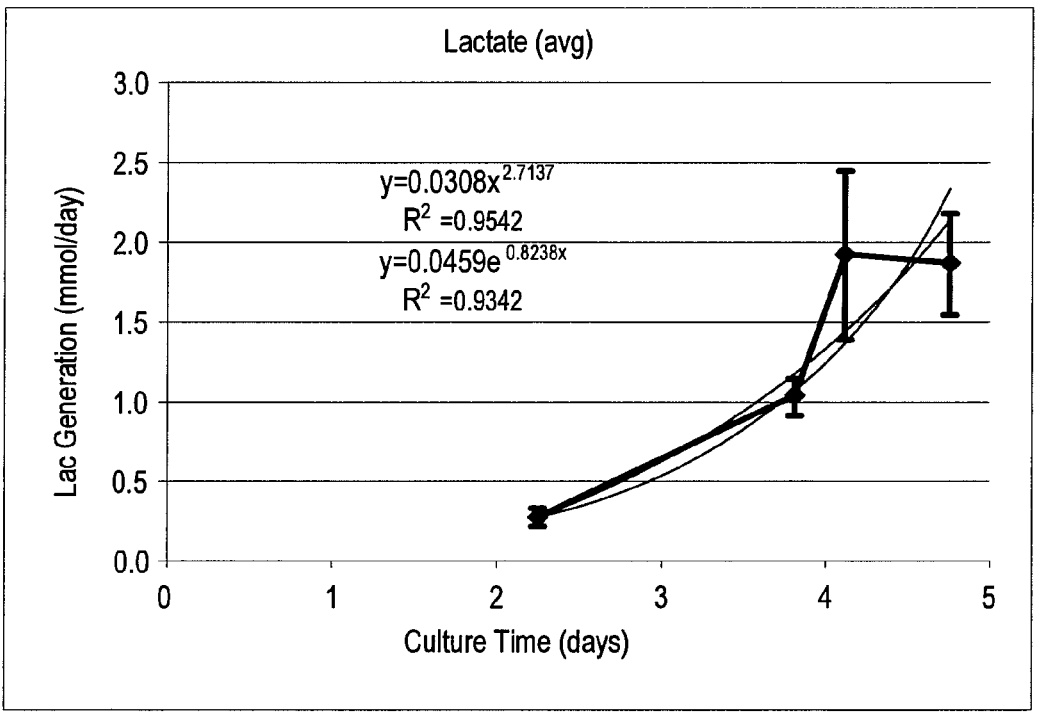
FIG. 20 is a graph showing average lactate generation during expansion after being loaded and distributed using previous methods.

FIGS. 19 and 20 illustrate data for cells loaded and distributed using previous methods. FIGS. 19 and 20 are provided for comparison. The fact that the best fit of the data in FIGS. 19 and 20 using regression analysis is the "power" regression line, is an indicator of a "constant" increase in lactate concentration. In contrast, there are exponential increases for methods consistent with embodiments of the present invention, as is illustrated in FIGS. 17 and 18.

Figure 21:
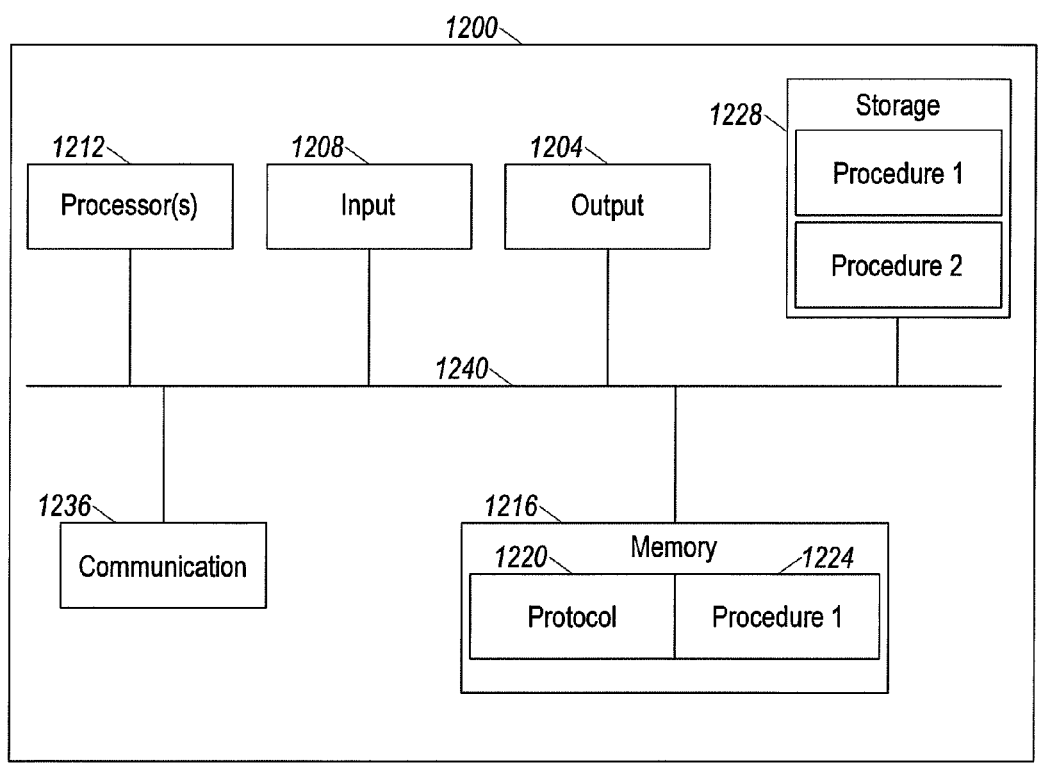
FIG. 21 illustrates a block diagram of a basic computer that may be used to implement embodiments of the present invention.

Finally, FIG. 21 illustrates example components of a basic computer system 1200 upon which embodiments of the present invention may be implemented. Computer system 1200 may perform some steps in the methods for loading and distributing cells. System 1200 may be a controller for controlling features, e.g., flow control devices, pumps, valves, rotation of bioreactors, etc., of CES systems 10, 800, and 900 shown above in which cells are loaded and distributed for expansion.

Computer system 1200 includes output device(s) 1204, and/or input device(s) 1208. Output device(s) 1204 may include one or more displays, including CRT, LCD, and/or plasma displays. Output device(s) 1204 may also include a printer, speaker, etc. Input device(s) 1208 may include a keyboard, touch input devices, a mouse, voice input device, etc.

Basic computer system 1200 may also include a processing unit 1212 and/or a memory 1216, according to embodiments of the present invention. The processing unit 1212 may be a general purpose processor operable to execute instructions stored in memory 1216. Processing unit 1212 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits.

The memory 1216 may include any tangible medium for short-term or long-term storage for data and/or processor executable instructions, according to embodiments. The memory 1216 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc. In embodiments, system 1200 may be used to control the rotation of bioreactor 300 and/or various flow control devices, pumps, valves, etc. of CES systems. Memory 1216 can store protocols 1220 and procedures 1224, such as protocols and procedures for loading and distributing cells in a bioreactor, which would control operation of circulation pumps, valves, rotation of bioreactors, etc.

Storage 1228 may be any long-term data storage device or component. Storage 1220 may include one or more of the systems described in conjunction with memory 1216, according to embodiments. Storage 1228 may be permanent or removable. In embodiments, system 1200 is part of a CES system and storage 1228 may store various protocols for utilizing the CES systems.

Various components may be referred to herein as "operably associated." As used herein, "operably associated" refers to components that are linked together in operable fashion, and encompasses embodiments in which components are linked directly, as well as embodiments in which additional components are placed between the two linked components.

The one or more present inventions may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The one or more present inventions, in various embodiments, include components, methods, processes, systems and/or apparatus substantially as depicted and described herein, including various embodiments, subcombinations, and subsets thereof. Those of skill in the art will understand how to make and use the present invention after understanding the present disclosure.

The one or more present inventions, in various embodiments, include providing devices and processes in the absence of items not depicted and/or described herein or in various embodiments hereof, including in the absence of such items as may have been used in previous devices or processes (e.g., for improving performance, achieving ease and/or reducing cost of implementation).

The foregoing discussion of the one or more present inventions has been presented for purposes of illustration and description. The foregoing is not intended to limit the one or more present inventions to the form or forms disclosed herein. In the foregoing Detailed Description for example, various features of the one or more present inventions are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the one or more present inventions.

Moreover, though the description of the one or more present inventions has included description of one or more embodiments and certain variations and modifications, other variations and modifications are within the scope of the invention (e.g., as may be within the skill and knowledge of those in the art, after understanding the present disclosure). It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of loading a plurality of cells in a cell expansion system, the method comprising:
    adding the plurality of cells to a fluid circulating at a first rate through a first fluid flow path and a bioreactor of the cell expansion system, wherein the first fluid flow path comprises opposing ends, a first opposing end associated with an inlet of the bioreactor and a second opposing end associated with an outlet of the bioreactor;
    maintaining the circulation rate of the fluid at the first rate for a predetermined period of time to uniformly distribute the plurality of cells;
    after the plurality of cells have been uniformly distributed:
    reducing the circulation rate of the fluid to a reduced rate that is less than the first rate; and
    allowing a predetermined period of time to pass so that a first percentage of the plurality of cells comprising less than or equal to about 80 percent of the plurality of cells settle in the bioreactor and a second percentage of the plurality of cells settle outside of the bioreactor in the first fluid flow path;
    expanding the first percentage of cells in the bioreactor; and
    wasting the second percentage of cells.

2. The method of claim 1, wherein the first percentage comprises less than or equal to about 80 percent of the plurality of cells and greater than or equal to about 50 percent of the plurality of cells.

3. The method of claim 1, wherein the first rate is greater than or equal to about 25 ml/min.

4. The method of claim 1, wherein the first rate is greater than or equal to about 25 ml/min and less than or equal to about 350 ml/min.

5. The method of claim 1, wherein during the maintaining:
    rotating the bioreactor around a rotational axis from a first orientation to a second orientation;
    pausing the bioreactor at the second orientation for a first period of time;
    rotating the bioreactor back around the rotational axis to the first orientation; and
    pausing the bioreactor back at the first orientation for a second period of time.

6. The method of claim 5, wherein the second period of time is substantially equal to the first period of time.

7. The method of claim 5, wherein the bioreactor has a longitudinal axis LA-LA, and wherein when the bioreactor is in the first orientation the longitudinal axis LA-LA is substantially perpendicular to the longitudinal axis LA-LA when the bioreactor is in the second orientation.

8. The method of claim 5, wherein the bioreactor has a longitudinal axis LA-LA, and wherein the longitudinal axis LA-LA is substantially horizontal when the bioreactor is in the first orientation and substantially vertical when the bioreactor is in the second orientation.

* * * * *